United States Patent [19]

Kemp et al.

[11] Patent Number: 5,536,648
[45] Date of Patent: Jul. 16, 1996

[54] AMPLIFIED DNA ASSAY USING A DOUBLE STRANDED DNA BINDING PROTEIN

[75] Inventors: David J. Kemp, North Balwyn; Simon J. Foote, Flemington; Michael G. Peterson, Lower Templestowe; Nicholas Samaras, Caulfield, all of Australia; Donald Smith, Berwickshire, Scotland

[73] Assignee: Amrad Corporation Limited, Victoria, Australia

[21] Appl. No.: 229,056

[22] Filed: Apr. 18, 1994

Related U.S. Application Data

[63] Continuation of Ser. No. 689,287, filed as PCT/AU89/00526, Dec. 8, 1989, published as WO90/06374, Jun. 14, 1990, abandoned.

[30] Foreign Application Priority Data

Dec. 9, 1988 [AU] Australia ................................. PJ1889
Jul. 4, 1989 [AU] Australia ................................. PJ5080

[51] Int. Cl.$^6$ .......................... C12P 19/34; C07H 21/04
[52] U.S. Cl. .................... 435/91.2; 536/24.33; 435/6; 435/7.1; 435/975; 935/77
[58] Field of Search ....................... 435/6, 7.1, 7.5, 435/91.2; 536/24.33

[56] References Cited

U.S. PATENT DOCUMENTS 4,623,627 11/1986 Huang ....................................... 435/240
4,978,608 12/1990 Kung et al. ................................. 435/6

FOREIGN PATENT DOCUMENTS 1193788 9/1988 Australia.
0223618 5/1987 European Pat. Off..
0224126 6/1987 European Pat. Off..
0357011 3/1990 European Pat. Off..
0370694 5/1990 European Pat. Off..

OTHER PUBLICATIONS

Hope, IA et al. Cell 43:177–188 Nov. 1985 "GCN4 Protein ..."
Mullis, K. et al. Cold Spring Harbor Symp. Quant. Biol. vol. LI:263–273. 1986.
Yamane, A. et al. Nucl. Acids Res. Symp. Ser 20:91–92 1988.
Smith, D. B. & Johnson Gene 67:31–40 1988.
Stahl, et al. (1988) "Solid Phase DNA Sequencing using the Biotin–Avidin System" *Nucleic Acids Research* 16, 3025–3038.
Syvanen, et al. (1988) "Quantification of Polymerase Chain Reaction Products by Affinity–Based Hybrid Collection" *Nucleic Acids Research* 16, 11327–11338.
Yamane, et al. (1988) "Rapid Detection of Specific Gene Sequences" *Chemical Abstracts* 109, 219.
Triglia et al. (1990) "Colourimetric detection of PCR products using the DNA binding protein TyR", Nucl. Acids Res. 18(4): 1080.
Goldstein et al. (1976) "The Chemistry of Enzyme Immobilization", in Applied Biochemistry and Bioengineering, vol. 1–Immobilized Enzyme Principles, Wingard et al., eds., Academic Press, pp. 23–126.

*Primary Examiner*—Garnette D. Draper
*Assistant Examiner*—Lorraine M. Spector
*Attorney, Agent, or Firm*—Scully, Scott, Murphy & Presser

[57] ABSTRACT

A method for capturing amplified target DNA on a solid substrate comprising incorporating a ligand into said DNA by a polymerase chain reaction using a set of primers wherein one of the primers bears the ligand, and contacting the so treated DNA with a solid substrate having a binding reagent for said ligand immobilized thereon.

38 Claims, 11 Drawing Sheets

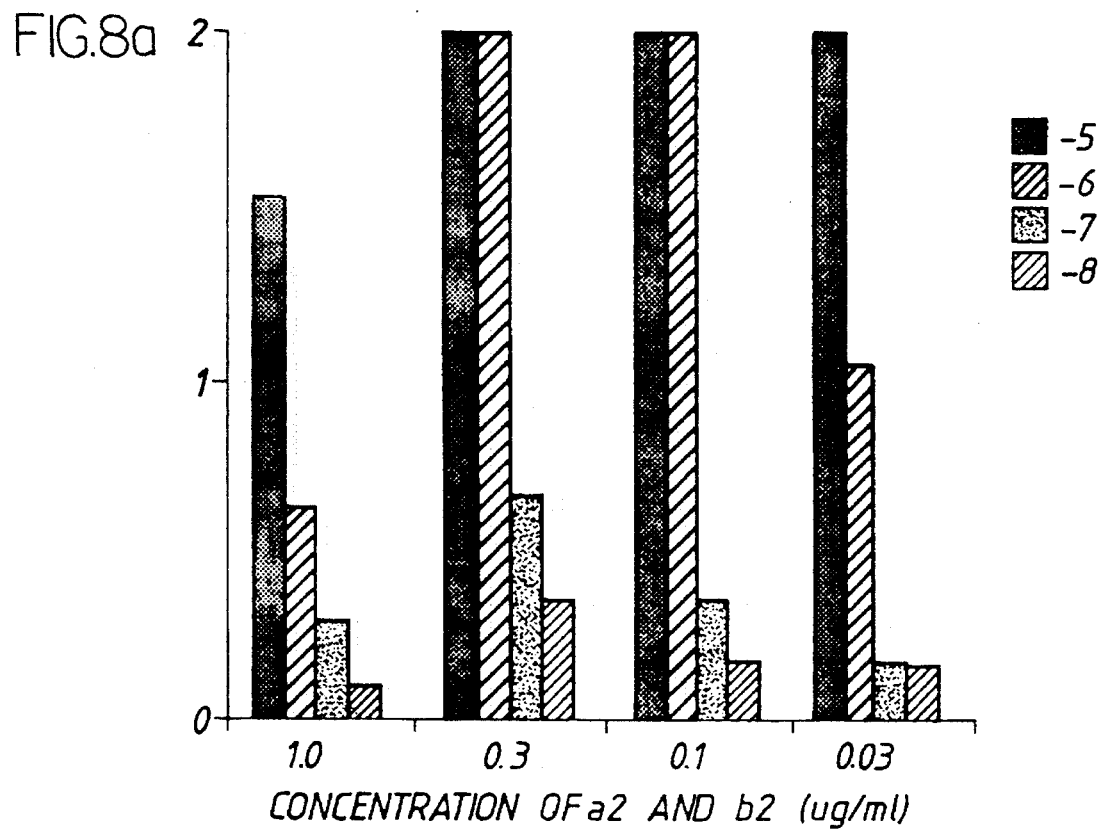
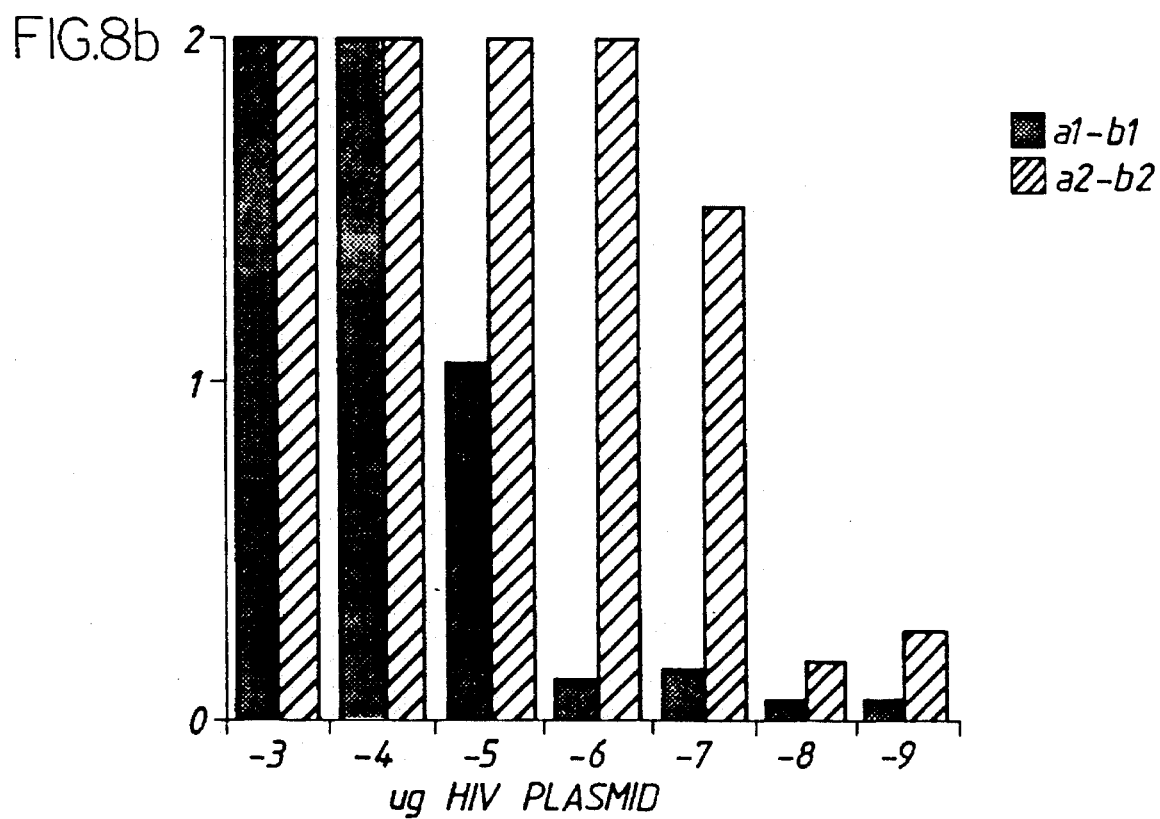

5,536,648

AMPLIFIED DNA ASSAY USING A DOUBLE STRANDED DNA BINDING PROTEIN

This is a continuation of application Ser. No. 07/689,287 filed on Aug. 1, 1991, now abandoned, which was a continuation of International Application PCT/AU89/00526 filed on Dec. 8, 1989 and which designated the U.S.

The present invention relates generally to the capture and detection of amplified target DNA in a sample. More particularly, the present invention relates to a single or multi-step amplified DNA assay (ADA) and the use thereof in the rapid capture and detection of target DNA in a sample, such as in the detection of a pathogen.

The polymerase chain reaction (PCR) system (1, 2) for amplifying specified segments of DNA has already proved to be of great value in experimental biology (1–8, see also Australian Patent Applications Nos. 55322/86, 55323/86, 69962/87 and 77298/87 in the name of Cetus Corporation) In the PCR procedure, a sample containing the DNA of interest is repetitively cycled through three temperatures. This results successively in denaturation of the DNA, annealing of synthetic oligonucleotides at the boundaries of the sequence of interest and the extension of the oligonucleotides by the DNA polymerase from *Thermus aquaticus* (Taq) (2). The exponentially amplified DNA segment can then be detected by simple procedures such as staining with ethidium bromide after agarose gel electrophoresis, or by hybridisation or sequencing to ensure that it is the expected sequence (1–6).

The PCR system should rapidly replace conventional procedures in many areas of mass screening (7). One of these is the detection of pathogens because of the generality of the technique and its exquisite sensitivity. Testing blood samples for human immunodeficiency virus (HIV) sequences is one such area in which preliminary studies have been reported (8). Other areas include epidemiology and human genetic applications such as HLA typing and screening for genetic diseases. However, current procedures for detection of the products of PCR reactions are not well suited to mass screening as they generally require gel electrophoresis. Further, artifactual DNA molecules resulting from such events as dimerization of the primers or misincorporation of primers into irrelevant sequences can readily arise and so hybridisation or sequence information is necessary to identify a molecule with certainty. Hence, an assay system for detecting DNA amplified by the PCR procedure that is highly specific, rapid, readily applicable to mass screening, suitable for any known sequence and uses equipment already available in many laboratories would be advantageous.

The present invention relates to an amplified DNA assay enabling the capture detection of target DNA in a sample. The assay may be accomplished in one or more steps.

Accordingly, the present invention contemplates a method for capturing amplified target DNA on a solid substrate comprising incorporating a first ligand into said DNA by a polymerase chain reaction using a set of primers wherein one of the primers bears the ligand and contacting the so treated DNA with a solid substrate having a binding reagent for said ligand immobilized thereon.

The present invention further contemplates the detection of said captured DNA by contacting said immobilized amplified DNA with a detection reagent which is capable of binding to a second ligand previously incorporated into said amplified DNA by the polymerase chain reaction using a set of primers wherein one of the primers bears the ligand capable of binding to a detection reagent.

Accordingly, the present invention contemplates a method for the detection of target DNA in a sample comprising optionally amplifying said DNA by the polymerase chain reaction and detecting a ligand or label incorporated into said DNA after said DNA has been immobilized onto a solid substrate.

In one embodiment, the present method first optionally amplifies target DNA by the polymerase chain reaction procedure using a first set of oligonucleotide primers selected to be complementary to the strands of said target DNA. The first PCR is optional to the extent that there may be an amount of target DNA sufficient to enable the practitioner to proceed to the next step without a first amplification. The target DNA, amplified or not, is amplified by the polymerase chain reaction procedure using a second set of oligonucleotide primers, the primers of said second set being selected to be complementary to the strands of said target DNA and being nested between the primers of said first set and wherein one of the primers of said second set bears a first ligand and the other of the primers of said second set bears a second ligand or a label. The amplified DNA is contacted to a solid substrate having a binding reagent for said first ligand immobilized thereon.

Another aspect of the present invention relates to a method for detecting target DNA, said DNA optionally amplified by a first polymerase chain reaction using a first set of oligonucleotide primers selected to be complementary to the strands of said target DNA, said method comprising subjecting said amplified DNA to a second polymerase chain reaction using a second set of oligonucleotide primers selected to be complementary to the strands of said target DNA and being nested between the primers of said first set and wherein one of the primers of said second set bears a first ligand and the other of the primers of said second set bears a second ligand or a label, contacting the amplified DNA with a solid substrate having a binding reagent for said first ligand immobilized thereon and then detecting the second ligand or label to indicate the presence of amplified DNA bound to said solid substrate.

Yet another aspect of the present invention is directed to a test kit for detecting target DNA in a sample by the amplified DNA assay comprising in compartmental form, a first container adapted to contain the reagents for a optional polymerase chain reaction and capable of receiving said target DNA including said first and/or optionally second sets of oligonucleotide primers; a second container adapted to contain said second set of oligonucleotide primers and the reagents for a second polymerase chain reaction when not carried in said first container; a solid substrate coated with a binding reagent; and a means for detecting amplified DNA bound to said solid substrate.

Still another aspect of the present invention relates to an amplified DNA assay for the detection of target DNA in a sample, which assay comprises the steps of:

a. optionally amplifying said target DNA, if present in said sample, by the polymerase chain reaction procedure using a first set of oligonucleotide primers selected to be complementary to the strands of said target DNA;

b. amplifying or further amplifying the product of step a. by the polymerase chain reaction procedure using a second set of oligonucleotide primers, the primers of said second set being selected to be complementary to the strands of said target DNA and being nested between the primers of said first set, and wherein one of the primers of said second set bears a first ligand and the other of the primers of said second set bears a second ligand or a label;

c. contacting the amplified product of step b. with a solid substrate having a binding reagent for said first ligand immobilised thereon; and d. detecting the second ligand or label to indicate the presence of amplified DNA bound to said solid substrate.

In further accordance with the present invention, steps (a) and (b) above can occur in either a single reaction mixture or two successive reaction mixtures.

In another aspect of the present invention, the target DNA may be subjected directly to one or more cycles of PCR using the labelled second set of primers and then subjected to binding to the said substrate. This would be particularly useful where there is an abundance of target DNA and/or where the detection means is very sensitive.

The following abbreviations are used in the present specification:

PCR Polymerase chain reaction
DNA Deoxyribonucleic acid
A Adenine
T Thymine
G Guanine
C Cytosine
GST Glutathione-S-transferase
ADA Amplified DNA assay
HIV Human immunodeficiency virus
TMB Tetramethylbenzidine
ABTS 2.2'-azino-bis-(3-ethylbenzthiazoline-6 -sulphonic acid)
MTPBS Mouse tonicity phosphate buffered saline
RT Room temperature
PBS Phosphate buffered saline In the accompanying drawings:

FIG. 1 shows the three basic steps of one embodiment of the ADA. In step 1, a DNA segment is amplified from a biological sample via oligonucleotides a and b. In step 2, specific ligands are incorporated into the amplified DNA segment through at least 3 further cycles of amplification via internally nested oligonucleotides. Oligonucleotide c. bears a molecule of biotin at its 5' terminus and oligonucleotide d. bears a 5' nucleotide sequence specifically recognised by the DNA binding protein, GCN4, of *Saccharomyces cerevisiae*. In step 3, ligand bearing DNA segments are bound to a solid support coated with purified GCN4 produced in bacteria (GST-GCN4) and are detected via binding of avidin-peroxidase to the biotin of oligonucleotide c. and subsequent colorimetric detection of peroxidase activity.

FIGS. 2a–c show the structure of yeast GCN4 and GST-GCN4. FIG. 2a shows the structure of the *Saccharomyces cerevisiae* GCN4 gene (9) with the coding region (281 amino acids) boxed and proposed transcription activation and DNA binding regions of the GCN4 protein indicated by hatching (10). Also indicated are the positions of oligonucleotides 1–3 used to amplify the GCN4 gene from yeast DNA by PCR. FIGS. 2a and 2b show the structure of genes encoding GST-GCN4 fusion proteins produced in *E. coli* by introducing fragments of the GCN4 gene into the plasmid expression vector pGEX-2T (11). The GCN4 gene was amplified from yeast DNA using oligonucleotides 2 and 3 or 1 and 3 to generate plasmids encoding partial (GST-GCN4 3.12) or full-length (GST-GCN4 6.8) versions of the GCN4 polypeptide fused to *Schistosoma japonicum* glutathione-S-transferase (GST).

FIG. 3a shows fractionation by polyacrylamide gel electrophoresis of total proteins (lanes 1 and 4) from *E. coli* strain 7118 transfected with plasmids pGST-GCN4 3.12 (lanes 1–3) or pGST-GCN4 6.8 (lanes 4–6) and grown in the presence of 0.1 mM IPTG for 1 hour at 37° C. Also shown is material purified from lysed bacteria by one-step affinity chromatography (lanes 3 and 6) and soluble proteins remaining after incubation with glutathione-agarose beads (lanes 2 and 5). FIG. 3b shows a gel retardation assay demonstrating that the mobility of a $^{32}P$ labelled DNA fragment containing a GCN4 binding site is decreased when it is mixed with purified GST-GCN4 3.12 (lanes 2 and 4) or GST-GCN4 6.8 (lane 6) in comparison to its mobility in the absence of protein (lane 1).

FIGS. 4a and 4b show the effect of added carrier DNA on the specificity of ADAs on DNA from HIV plasmid pHXBc2. In row A there was no added carrier DNA in the microtitre dish, while rows B, C and D contained 1 μg/ml, 0.1 μg/ml and 0.01 μ/ml of sonicated human DNA, respectively. Step 1 of the ADA was for 30 cycles as described in Example 1, below, using oligonucleotides a. and b. and a Sac1-Sal1 fragment from pHXBc2 (12). Samples (5 ml) from step 1 were then amplified for a further 10 cycles using oligonucleotides c. plus b. (columns 1–3), c. plus d. (columns 4–6) or c. plus d2 (columns 7–9). Samples (5 μl in 1, 4 and 7; 0.5 μl in 2, 5 and 8; 0.05 μl in 3, 6 and 9) were then added to wells of plates coated with purified GST-GCN4 3.12 (FIG. 4a) or GST-GCN4 6.8 (FIG. 4b). The remaining steps of the ADAs were as in Example 1.

FIG. 5 shows ADAs on DNA from HIV-infected cells. Samples 1–3, human DNA (~100 ng) from a Burkitt's lymphoma; samples 4–6, human DNA (~100 ng) from HIV-infected cells; samples 7–9, no DNA; samples 10–12, DNA (~1 ng) from plasmid pHXBc2. Step 1 of the ADA was for 35 cycles as described in Example 1 using oligonucleotides a. and b. Samples of 10 μl from step 1 were then amplified a further 6 cycles using oligonucleotides c. plus d. Samples (15 μl for 1, 4, 7 and 10; 3 μl for 2, 5, 8 and 11; and 0.6 μl for 3, 6, 9 and 12) were added to wells of plates coated with purified GST-GCN4 3.12 in the presence of sonicated human DNA (1 μg/ml). The remaining steps of the ADAs were as in Example 1.

FIG. 6A shows the specificity of the one step ADA reaction. Competition of unreacted biotinylated oligonucleotides with the ADA substrate in a one step binding reaction. A PCR was performed using oligonucleotides c1 and d1 (0.2 μg) with 1 ng of plasmid pHXBc2 in a 100 μl reaction mix, cycled 24 times. The control did not contain any plasmid DNA. For rows 1 and 3 the volumes of PCR reaction indicated were added to 50 μl of binding mix (without powdered milk) containing the dilutions of a 5 mg/ml avidin-peroxidase solution indicated. For rows 2 and 4, the volumes of PCR reaction indicated were added, and a further 8 μl of the control PCR was added to each well. The binding reactions and colour development are described in Example 3.

FIG. 6B shows the specificity of the one step binding reaction. The procedure was as for FIG. 6A, except that the wells contained the % (w/v) of non-fat powdered milk indicated. The top and bottom rows contained 5 μl/well of the PCR mix described above. For row 2, oligonucleotide d was omitted. For row 3, there was no DNA in the PCR. Row 4 was as for row 3, but an unrelated oligonucleotide (1 μg/ml) was added. For row 5, the wells were not coated with GCN4.

FIGS. 7a and 7b show the effect of annealing temperature on incorporation. PCRs were carried out with 1 ng plasmid pHXBc2 and oligonucleotides a1 and b1 (1 μg/ml), c2 and d2 (2 μg/ml) as indicated, and cycled under the conditions shown, 10 μl samples were fractionated on a 1.6% (w/v) agarose gel in the presence of 1 μg/ml ethidium bromide. For FIG. 7a the concentrations of a1 and b1 were 0.3 g/ml. For FIG. 7b the concentrations of oligonucleotides a1 and c1 in the PCR were the following in successive tracks: a1=6, 6, 2, 0.6, 2 μg/ml, b1=3 μg/ml, c1=20, 30, 10, 10, 20 μg/ml, d1=5 μg/ml.

FIG. 8A shows the sensitivity with different oligonucleotide concentrations. Two step PCRs were carried out with oligonucleotides a2 and b2 (concentrations as indicated) and c2 and d2 (5 μg/ml) with the amounts of Plasmid indicated (at the right in μg) in a 20 μl reaction, cycled 30 times (95°/30 sec, 65°/60 sec) and then 12 times (95°/30 sec, 40°/60 sec, 65°/30 sec). 5 μl of the product was then analysed in an ADA with a one-step binding reaction.

FIG. 8B shows the sensitivity of ADA reactions. Comparison of the sensitivity of ADA reactions using a and b oligonucleotides with different spacings from c2 and d2. The a and b oligonucleotides were at 0.3 μg/ml.

FIG. 9 shows the ADA dependence on temperature shift. Two step PCRs were carried out with oligonucleotides a2, b2, c2 and d2 as in FIG. 3B. The DNA was from $5 \times 10^3$ HIV-infected CEM cells. The PCRs were cycled at 95°/30 sec, 65°/60 sec for the number of cycles indicated by the arrows, and then at 95°/30 sec, 40°/60 sec, 65°/30 sec for 0, 5 and 10 further cycles. The number of cycles indicated at the bottom is the total number for each sample.

FIGS. 10a and 10b show the detection of HIV in cultured cells. DNA from uninfected or HIV-infected CEM cells was used as the input DNA for PCR reactions containing oligonucleotides a2 and b2 (0.3 μg/ml) and c2 (2.5 μg/ml) and d2 (5 μg/ml) that were cycled 30 times (95°/30 sec, 65°/60 sec) followed by a further 10 (top 3 rows in right panel) or 15 (bottom 3 rows in right panel, and left panel) cycles (95°/30 sec, 40°/60 sec, 65°/30 sec). Plasmid DNA was used as a positive control. ADA reactions with a one-step binding reaction were carried out on 5 μl samples, and agarose gel electrophoresis on 10 ml samples. The DNA samples analysed in the ADAs or by gel electrophoresis represented the material obtained from the number of cells indicated, or from the number of plasmid molecules indicated.

Figures 10A, 10B:
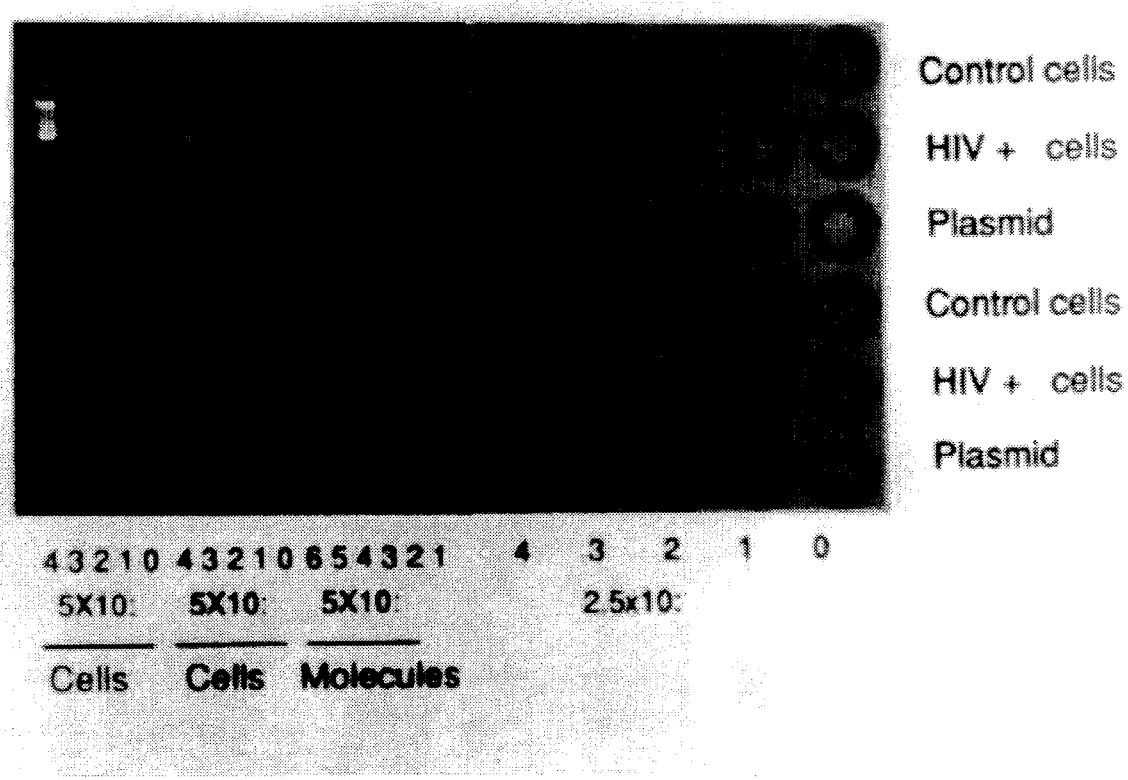
Figure 11A:
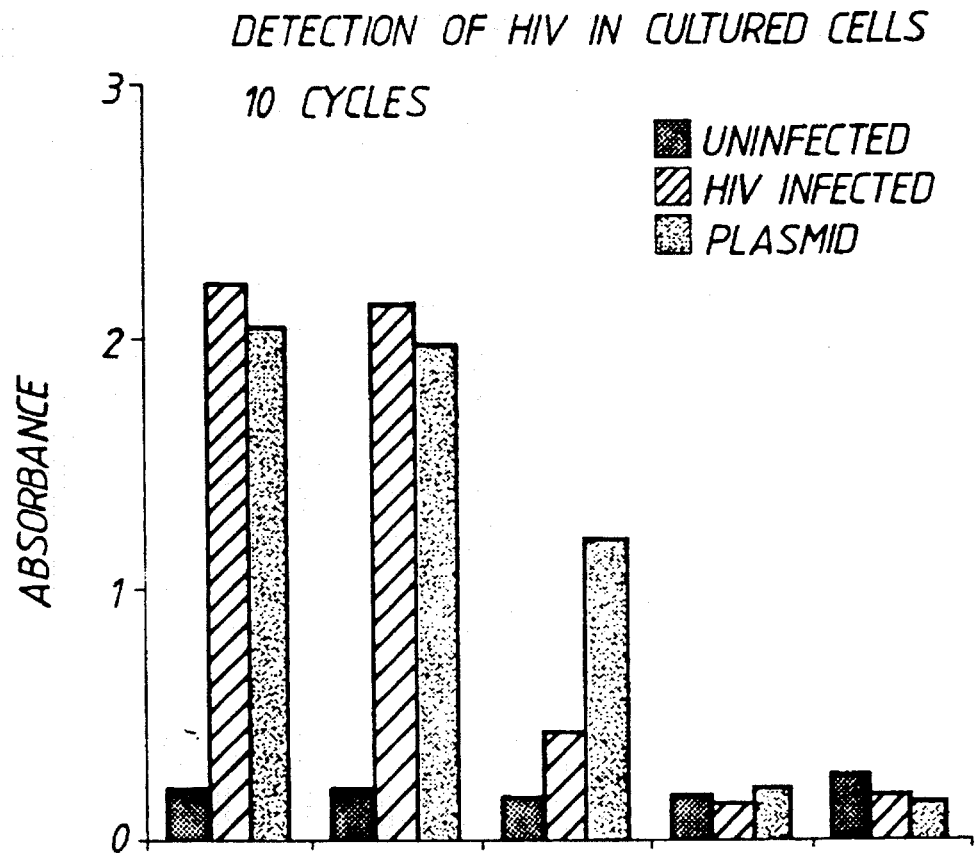
FIGS. 11a and 11b show the quantitation of the ADA reactions shown in FIGS. 10a and 10b.
Figure 11B:
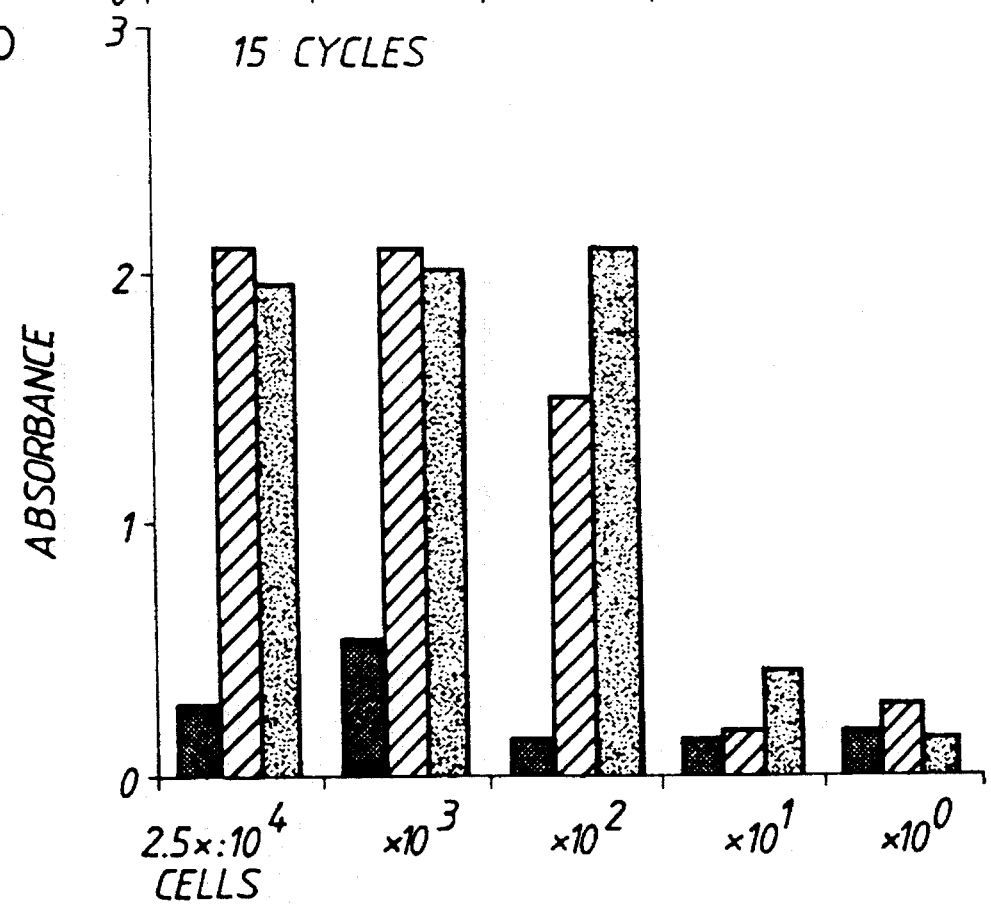
Figure 15:
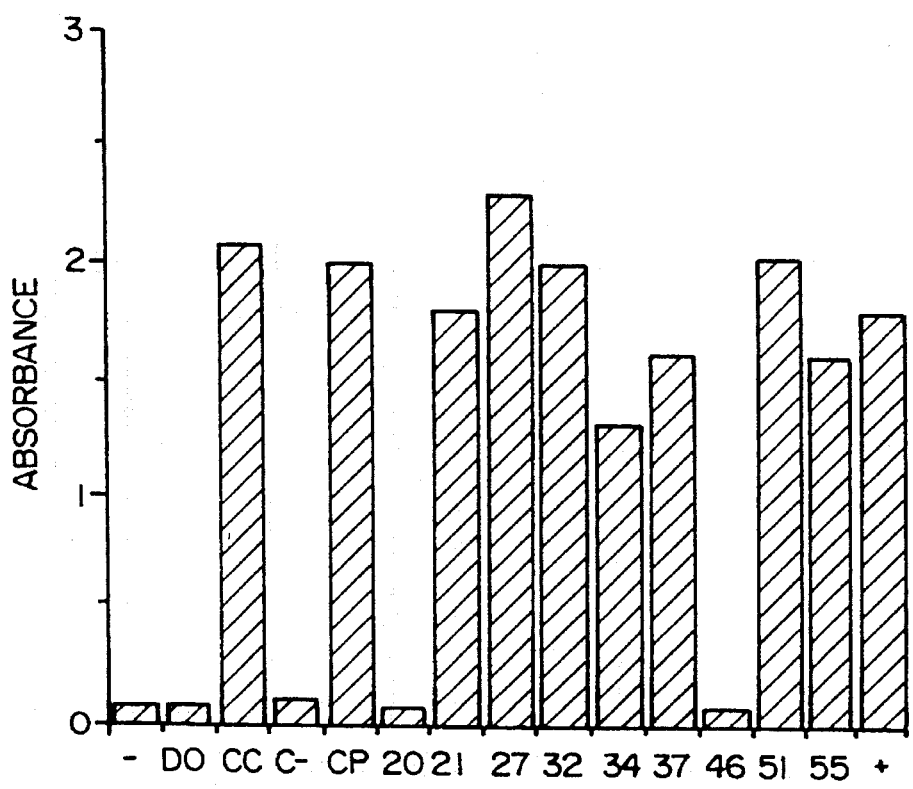

FIG. 15 shows the results of a clinical trial performed on Peripheral Blood Lymphocytes (PBL's) taken from patients positively diagnosed as suffering from AIDS or from negative controls. The method is as described in FIGS. 10a and 10b except 2 PCR's, 35 and 12 cycles respectively were used. Abbreviations are defined in Example 9.

In general terms, in one embodiment of the present invention, target DNA is first amplified by PCR using a first set of appropriate oligonucleotide primers in accordance with the known PCR procedure and then a second set of oligonucleotide primers, nested between the first two, are incorporated by a small number of additional cycles. The nucleotides in the second set of primers bear ligands, for example, one can be biotinylated and the other contain a site for a double stranded DNA binding protein. After linking to an immobilised affinity reagent, such as a DNA binding protein and labelling with a second affinity reagent, for example avidin linked to horseradish peroxidase, reaction with a chromogenic substrate allows detection of the amplified DNA. Furthermore, a system such as digoxigenin could be employed. Where there is sufficient target DNA without a first amplification or for other reason such as convenience or speed of assay, the target DNA may be directly subjected to incorporation by the labelled primers.

The assay procedure of the present invention is described in detail herein with particular reference to an assay for the detection of Human Immunodeficiency Virus (HIV) sequences. It will be understood, however, that this particular assay is described by way of exemplification of the invention and the invention has wider application as discussed below. Accordingly, by "target DNA" is meant any eukaryotic, prokaryotic or viral nucleic acid sequence and includes the identification of pathogens or the screening of human or other mammalian genetic disorders such as in cancer cells. Furthermore, target DNA encompasses RNA wherein by the action of reverse transcriptase, corresponding DNA is first synthesised, i.e. cDNA copied by reverse transcriptase from RNA. Target DNA also extends, therefore, to RNA viruses. Target DNA also extends to plant genetic sequences and to their pathogens.

Furthermore, the source of target DNA may vary depending on the particular circumstances and relative convenience. For example, one embodiment of the subject invention is described in terms of detecting HIV sequences in blood. However, this is done with the understanding these and other target sequences may be isolated from other bodily fluids such as, but not limited to, saliva. Accordingly, the present invention extends to the detection of target DNA in any suitable biological fluid such as blood, saliva, lymph fluid, cell and tissue extracts, culture supernatants, plant sap and/or other fluids or tissue extracts, aerosols, various environmental locations (e.g. soil, water, etc.) and the like.

The ADA procedure of this invention provides a very sensitive, specific, simple and convenient method for detecting specific DNA segments amplified by at least one PCR. The sensitivity of the method results from the combination of the inherent sensitivity of the PCR procedure itself (it can detect a single DNA molecule against a background of at least $10^6$ human genomes (2)) and a sensitive novel method for detecting the amplified DNA. The data below show that molecules of the ligand-containing amplified DNA can readily be detected and only a small fraction of the product from a typical PCR reaction is necessary for detection.

The specificity of the procedure reflects the fact that the ADA, in one embodiment, uses two successive PCR reactions with nested oligonucleotide primers. Only DNA molecules generated in the second step are detected in the final step because the ligands are only introduced during the second step. Alternatively, the target DNA may undergo the binding step directly without need of a first PCR. This specificity may be further increased, as in Example 2 herein, by the fact that GST-GCN4 only binds to double-stranded DNA—it does not recognise the single-stranded oligonucleotides. As the second step utilises only a small number of cycles (for example 3–12 cycles), there is insufficient time for accumulation of significant amounts of primer-dimers derived from the oligonucleotides of the second set or other double stranded DNA artefacts. Furthermore, any such artefacts generated in the first PCR step, for example by spurious priming at other places in the genome, are not amplified in the second step because they will not contain the nested sequences of the second set of primers. Primer-dimers formed in the first step will not be detected as they do not contain the ligands.

It is another embodiment of the subject invention that the PCR can be performed in one reaction mixture effectively resulting in a "single step ADA". This modification to the multi-step procedure previously outlined is predicated in part on a strong dependence of the thermal stability of an oligonucleotide duplex on its length and hence, oligonucleotide primers can be selected such that their incorporation in a PCR is critically dependent on the annealing temperature. Consequently, if one set of primers is considerably longer than a second set, then successive PCR reactions can be carried out in the one reaction mixture by incubating the mixture through first a high temperature and then a low temperature thermal cycle regime. (See Example 5).

The present invention, therefore, extends to both the multi-step and single step ADA.

The one step ADA also has advantages in the binding step where the binding of the amplified product to the binding reagent immobilized to a solid substance occurs simultaneously to the binding of or to a detection complex. In one embodiment, the amplified DNA is bound to GST-GCN4 immobilized in the wells of a microtitre dish while simultaneously binding to the avidin-peroxidase conjugate.

A further aspect of the one step ADA relates to the use of single or multiple beads or pins coated with a binding reagent to transfer the amplified product from a reaction vessel, after washing, and contacting immobilized amplified product to a detection complex, to detection substrate. For example, the amplified DNA is transferred from a microtiter well by an array of GST-GCN4-coated beads or pins and, after washing and contacting with avidin-peroxidase, the beads are immersed in a microtiter dish containing ABTS substrate.

The successive PCR reactions can be carried out in the one reaction mixture, simply by incubating the mixture through first a high temperature and then a low temperature thermal cycle regime. As the complete PCR mixture containing all 4 oligonucleotides and enzyme (minus sample DNA) for this can be stored frozen, the protocol becomes greatly simplified, namely (1) the DNA sample is added to the PCR mixture, a drop of paraffin oil is added and the tube is placed on a thermal cycler and subjected to the two successive thermal regimes; (2) a sample is then placed in the GST-GCN4-coated microtiter well for simultaneous immobilization and binding; and (3) the dish is then washed and substrate added. This protocol is well suited to handle moderate numbers of samples. For example, the results for 50 samples can be obtained about 1 hour after completion of the PCRs.

In the one step assay, the amplified DNA binds to GST-GCN4 immobilized in the wells of a microtiter dish while simultaneously binding to the avidin-peroxidase conjugate. This decreases both the number of manipulations required and the time taken in handling samples, with no decrease in sensitivity or specificity. However, unincorporated biotinylated oligonucleotides compete with the amplified DNA for binding to avidin and it is necessary to ensure that the amount of biotin does not exceed the binding capacity of the avidin.

Furthermore, the one step assay also provides a protocol where the PCR with two successive thermal regimes is itself performed in a modified microtiter dish. The amplified DNA molecules are then bound to GCN4 immobilized on polystyrene beads attached to the lid of a microtiter dish. While this procedure cannot take advantage of the simultaneous immobilization and avidin-peroxidase binding, it has the very considerable advantage that after pipetting individual DNA samples into the first microtiter well, 96 samples can be handled simultaneously in a manner analogous to the widely used "FAST ELISA" system.

In all of these systems, streamlining of the detection systems has now reached the point where the time spent on preparing and handling individual DNA samples is the rate limiting event. The less abundant the target sequence, the higher the degree of purification that will be necessary. If the target sequence is detectable in less than 1 μl of whole blood, then boiling the sample can be sufficient. However, if the required sensitivity demands that the total DNA from a large volume of blood is added to a single PCR, purification is required. It is self evident that this depends both in the intrinsic sensitivity of the assay (i.e., the number of relevant molecules than can be detected in an ideal situation) and the maximum amount of sample before inhibition of the system occurs. Blood seems to be a particularly bad DNA source because of the high protein content. Clearly, the minimal purification protocol necessary for a particular system is dependent on these parameters. Additionally, these modifications to the multi-step protocol described herein are capable of detecting HIV sequences against a background of human DNA.

The simplicity and convenience of the ADA results from the fact that after the PCR steps, the sample may be treated in precisely the same manner as a routine enzyme-linked immunosorbent assay (ELISA), using the same equipment. As the immobilisation by affinity binding to the solid phase (for example, GST-GCN4 or avidin) can be carried out in the same step as labelling at the other end of the DNA molecule (in the example, with avidin-peroxidase), the number of pipettings and washing is minimised. Further, if the solid phase coated with the affinity reagent consisted of pins in the roof of a microtitre dish, washing could be simplified. This latter approach also could readily lend itself to automation of the detection steps. The reactions in the example herein are extremely rapid because of the high affinities of avidin and GCN4 for their substrates, and the high Vmax of horseradish peroxidase.

The ADA system described in detail herein is only one possible formulation that has many alternatives. Obviously, the approach could be used for detection of many other viral, bacterial, protozoan, fungal and mycoplasmal pathogens. Screening for hepatitis, tuberculosis, malaria and candida infections are among the obvious applications involving these disparate organisms. Similarly, this system could be used for the detection of cellular disorders such as cancers and the like. The outstandingly useful feature of the ADA approach is that it is only necessary to change the sequences of the oligonucleotides in order to detect any gene from any organism by a simple colour test. If the length of the test DNA segment for each case is the same, then the kinetics of the detection steps should be identical as the same affinity reagents are interacting with the same ligands in all cases. This contrasts with the ELISA system where the affinity and kinetics are determined by the monoclonal antibodies, which differ for each situation. Another potential application lies in determining the genotypes of certain pathogens. For example, in *Plasmodium falciparum*, some genes contain variable regions defining different antigenic determinants surrounded by relatively conserved regions (13). If the probes of the first set of primers corresponded to such flanking conserved regions, the products of the first PCR step could be tested with several pairs of oligonucleotides corresponding to internal variable regions that define the different serotypes. The ADA described herein is also applicable to screening for genetic diseases such as cystic fibrosis and cancers amongst others.

The ADA system of the present invention could in theory employ a wide variety of ligands and/or affinity reagents. In one embodiment, the double-stranded DNA—specific DNA binding protein is of the leucine zipper type i.e. GCN4. A range of other DNA binding proteins of this type could be used, including thrombin-cleaved GCN4 (FIGS. 2a–c, 14). Accordingly, the present invention extends to leucine zipper type DNA binding proteins such as GCN4 and/or its derivatives which includes GST-GCN4, thrombin-cleaved GCN4 and any other modifications thereof such as additions, deletion and/or substitution to the GCN4 amino acid and/or carbohydrate moieties provided said derivatives retain DNA binding activity Another DNA binding protein that could be used in the ADA is the TyrR protein of the "Helix turn Helix" type and which has a C-terminal DNA binding domain (Dr V. Argyropolous, Thesis submitted for degree of Doctor of Philosophy, The University of Melbourne, Parkville, Victoria, Australia). Other DNA binding proteins which may be used in the ADA are well known and include, for example, the "zinc finger" type. These binding proteins are reviewed by Struhl (19). Furthermore, an alternative to biotin would be a simple chromophore or a fluorescent dye. In this variation, the increase in specificity that comes from the ability of such DNA binding proteins to discriminate between double stranded (i.e. incorporated) and single stranded (i.e. unincorporated) oligonucleotides would be lost. This could be acceptable in many situations as there is already considerable specificity in the reactions.

As well as the applications to pathogens such as HIV used to develop the system here and the applications to genotyping pathogens mentioned above, the ADA system could be used with appropriate modification for virtually any application amenable to PCR itself (see for example references (1) to (8) and the Australian Patent Applications cited above). Major examples would include human genetics applications such as HLA typing and prenatal diagnosis of genetic disorders. The simplicity, specificity and generality of the approach should find many other applications.

Another embodiment of the subject invention employs a single PCR to incorporate directly label and/or ligand bound primers into target DNA without first being amplified and then exposing labelled target DNA to the solid support prior to, or simultaneously to, detection. This provides an even more streamlined method of detecting target DNA and makes the first PCR an optional step depending on the circumstances.

The present invention also extends to a conjugate consisting essentially of a support, a DNA binding protein and preferably a double-stranded DNA-specific DNA binding protein and more preferably GST-GCN4 or TyrR immobilized on said support and an amplified double-stranded DNA bound at a first end to said binding protein, such as to GST-GCN4. The conjugate further comprises at the second end of said double-stranded DNA, a label and preferably said label is an enzyme. In one embodiment the label is conjugated to the amplified DNA through an avidin-biotin bridge.

The present invention is further described by the following non-limiting examples.

EXAMPLE 1

MULTI-STEP ADA

Materials and methods

Isolation and expression of the GCN4 gene from *S. cerevisiae*.

Figure 2A:
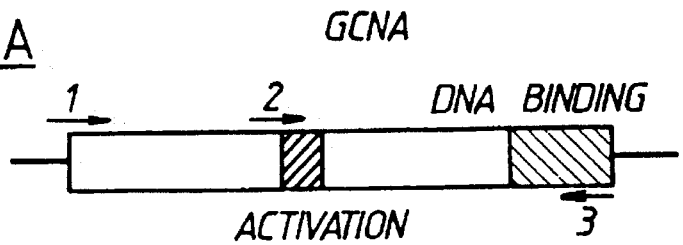

The complete coding region of the GCN4 gene from *S. cerevisiae* (9) was synthesized by PCR on a crude DNA preparation using oligo 1 (GGAATTCTAATGTC-CGAATATCAGCCA) and oligo 3 (GGAATTCAGCGT-TCGCCAACTAATTTC) of GCN4, and incorporating EcoRI sites at their 5' terminii (FIG. 2a). After cleaving with EcoRI, the DNA was ligated to EcoRI cut DNA of the expression vector pGEX-2T (11). A smaller portion of GCN4 was also isolated by PCR using oligo 3 above and oligo 2 (CGGATCCATGTTTGAGTATGAAAACC) containing a BamHI site at the 5' terminus (FIG. 2a) and insertion of the PCR product after cleavage with BamHI and EcoRI into BamHI and EcoRI cut pGEX-2T DNA.

Gel retardation assay

Gel retardation was carried out as described (15) on 7.5% (w/v) polyacrylamide gels except that no blocking DNA was present. The substrate for binding was made by annealing 40 ng each two oligonucleotides (CCACCTAGCGGATGACT-CATTTTTTTTCTTAGCG and CGCTAAGAAAAAAAAT-GAGTC) and incubating them with Taq DNA polymerase (Cetus) in a reaction mix identical to that used for PCR except that dATP was replaced by 20 mCi $a^{32}$P-dATP (Amersham). After 5 minutes at 70° C. dATP was added to 0.25 mM and the incubation continued for 5 minutes. Unincorporated $a^{32}$P-dATP was removed by passage through a Sephadex G-10 spin column.

Amplification of HIV Sequences—Step 1.

PCR reactions for amplification of p24 sequences from DNA isolated from HIV infected cells contained 50 mM KCl, 10 mM Tris pH 8.4, 2.5 mM $Cl_2$, 0.25 mM each dATP, dCTP, dGTP and dTTP, 0.01% gelatin, 1.5 units Taq DNA polymerase (Cetus), 4 ng oligonucleotide primers a. and b. and 100 ng purified DNA. Reaction mixes (100 ml) were cycled approximately 30 times between 40° C., 70° C. and 95° C. for 1.5, 2.0 and 1.5 minutes respectively.

Incorporation of Ligands—Step 2.

One-tenth of a Step 1 PCR reaction was subjected to at least 3 additional cycles of PCR under identical conditions except that the primers used were oligonucleotides b. and c., c. and d. or c. and d1.

Sequence of Oligonucleotides

The sequences (12) of the oligonucleotides corresponding to the p24 gene of HIV used were:

a.     AGAGAACCAAGGGGAAGTGA     (positions 1481–1500)

b.     TCTCTAAAGGGTTCCTTTGG     (positions 1661–1680)

c.     CATAGCAGGAACTACTAGTA     (positions 1501–1520). Oligonucleotide c. was biotinylated at the 5' end.

d. AAGTGACTCAAGTGACTCAA/TCCTTGTCTTAT-GTCCAGAA (nucleotides 5' to the slash correspond to an artificial GCN4 binding site (14), while those 3' to the slash correspond to positions 1641–1660).

d1. AGCGGATGACTCATTTTTTTT/TCCTTGTCT-TATGTCCAGAA (nucleotides 5' to the slash correspond to an artificial GCN4 binding site (14), while those 3' to the slash correspond to positions 1641–1660).

Preparation of DNA from HIV-infected cells.

CEM cells were derived by culturing human peripheral blood cells from a patient with acute lymphoblastic leukaemia, and then infected with HTLV IIIb. DNA was purified using guanidine HCl and CsCl centrifugation.

Detection of Amplified DNA—Step 3.

Microtiter trays (Dynatech Laboratories Inc.) were coated with purified GST-GCN4 fusion polypeptides at approximately 1 μg/ml in mouse tonicity phosphate-buffered saline (MTPBS) for 3 hours at 37° C. (50 μl per well) and then blocked with 1% (w/v) bovine serum albumin (fraction V) (Flow Laboratories) in MTPBS for 1 hour at 37° C. Trays were then washed with MTPBS containing 0.05% (v/v) Tween-20 (MTPBS-Tw-20) and twice with MTPBS alone, before incubation at 20° C. for 30 minutes with 50 μl of ligand bearing DNA diluted in MTPBS-Tw-20. Trays were washed as before and incubated again at 20° C. for 30 minutes with 50 μl horseradish peroxidase-avidin D conjugate (Vector Laboratories, Inc.) at a concentration of 2.5 μg/ml in MTPBS-Tw-20. After washing once in MTPBS-Tw-20 and four times in MTPBS, 100 μl of fresh 0.1M citrate pH 4.2 containing 1 mM 2,2'-azino-bis(3-ethylbenzthiazoline-6 -sulphonic acid) and 0.1% hydrogen peroxide were added to each well and absorbance read in a Titertek Multiskan MCC/340 scanner using filters of 414 nm and 492 nm.

EXAMPLE 2

Results of Multi-Step ADA a. The three basic steps of the ADA.

Figure 1:
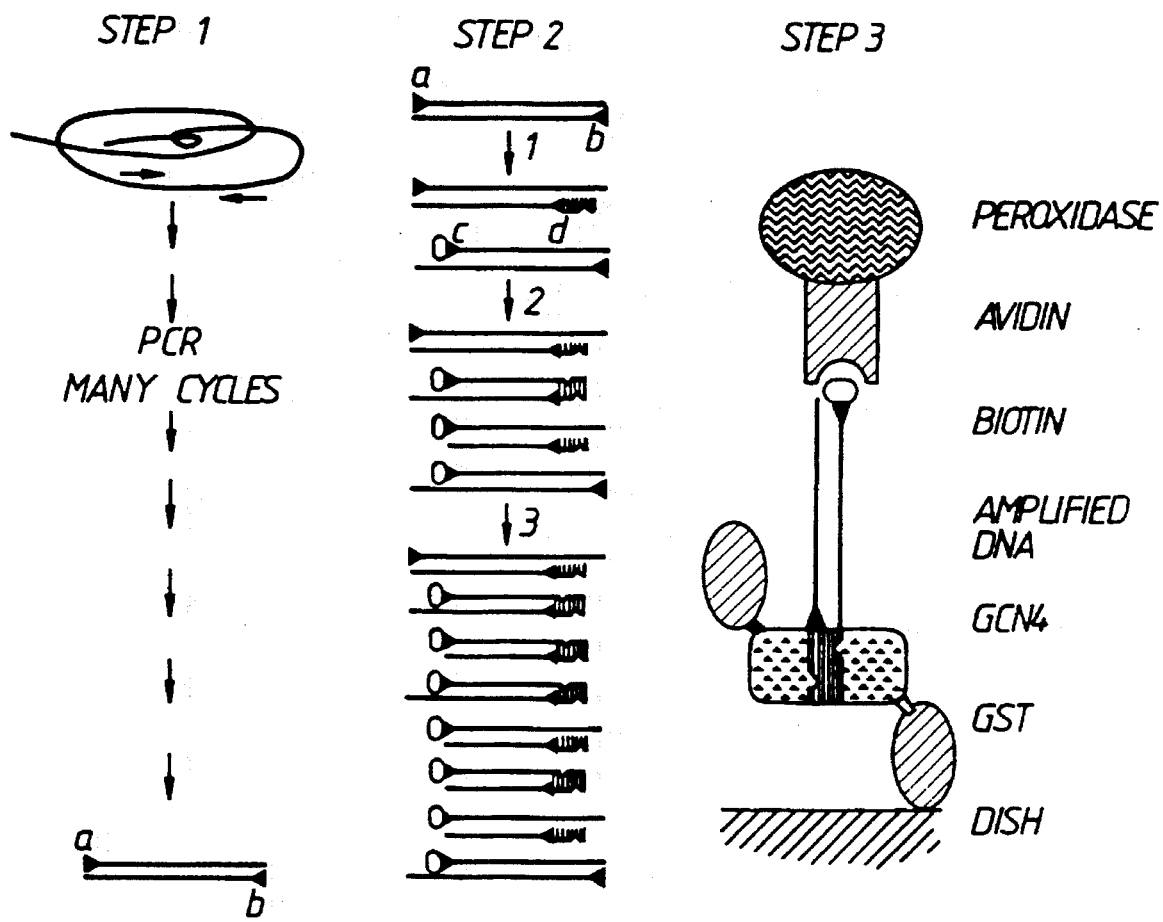

The approach to the detection of specifically amplified DNA is outlined in FIG. 1. The ADA consists of three basic steps, the first two of which are different PCR reactions performed successively. A sample of the amplified DNA is then placed in a well of a microtitre dish for detection. As described above, there are many different possible permutations of the ADA of varying specificity and simplicity. For the sake of clarity, only one example of the theoretically most specific formulation is described in this section.

Step 1: Amplification.

This step is simply a standard PCR reaction performed on any suitable DNA-containing extract relevant to the sequence of interest, for a large number of cycles. The oligonucleotides for step 1 (designated a and b in FIG. 1) are limiting for this reaction. Step 1 simply amplifies the desired segment of DNA.

Step 2: Sequence-specific ligand incorporation.

This step achieves specificity and simultaneously incorporates ligands into the PCR products that can react with affinity reagents, and thereby be detected in step 3. For step 2, two new oligonucleotides (designated c and d in FIG. 1) are used for a second PCR reaction that can be cycled for as little as three cycles. This achieves specificity because oligonucleotides c and d are nested between oligonucleotides a and b. There are only a small number of cycles and therefore the only molecules that will form to a detectable extent are those generated by amplification of the correct sequence in step 1. Step 2 also incorporates the ligands. This can be done either as shown for oligonucleotide c, which is biotinylated, or as shown for oligonucleotide d which contains extra sequences encoding the recognition site for a double-stranded DNA binding protein, such as the yeast regulatory protein GCN4 (14). At least three cycles of step 2 are necessary to generate blunt-ended molecules with these ligands at both ends (FIG. 1).

Step 3: Anchoring and enzyme-linked-labelling of the amplified DNA by affinity binding.

This step attaches the amplified DNA to a solid phase by affinity binding at one end, and is followed after washing by attachment of an enzyme by affinity binding at the other end for subsequent colour generation. For step 3, a sample from step 2 is added to a well of a microtitre dish. The well has been pre-coated with one of the affinity reagents, for example a cloned fused polypeptide bearing DNA binding protein GCN4 (see below). This polypeptide specifically immobilises the amplified molecules because of its affinity for double stranded DNA containing the correct sequence, incorporated via oligonucleotide d. After washing, a solution of the other affinity reagent conjugated to an enzyme, for example avidin linked to horseradish peroxidase, is added. This binds to the biotin linked to oligonucleotide c. As is evident, the locations of the two affinity reagents could readily be swapped (see below).

After washing, a chromogenic substrate is added to the microtitre dish, allowed to develop and the absorbance is read in a microtitre-plate reader.

b. Generation of a DNA binding protein that can be readily purified.

Figure 2B:
Figure 2C:
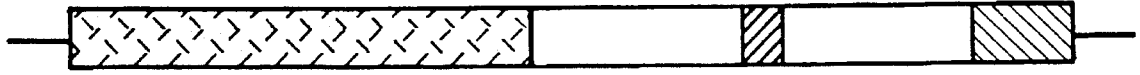
Figures 3A, 3B:
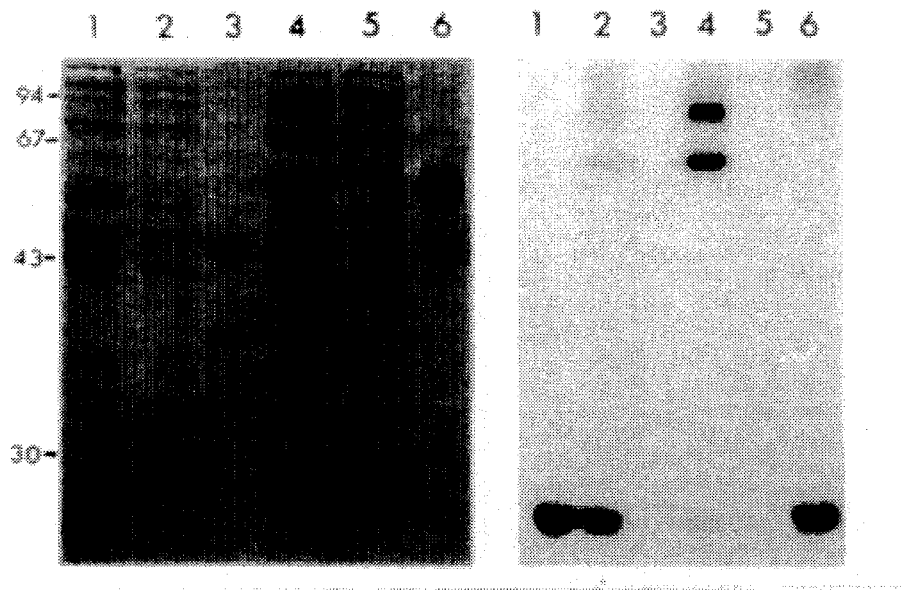

In order to generate large amounts of a high-affinity DNA binding protein suitable for routine use in the ADA, the *Saccharomyces cerevisiae* regulatory protein GCN4 has been expressed as a glutathione-S-transferase (GST) fusion protein as shown in FIGS. 2b and 2c. Plasmid pGST-GCN4-3.12 contains most of the sequence of GCN4 from *Saccharomyces cerevisiae*, including the C-terminal DNA-binding region, inserted into the plasmid pGEX-2T (11), while the plasmid pGST-GCN4-6.8 contains the entire coding sequence of GCN4. At the N-terminus, the GST-GCN4 fused polypeptide contains the entire sequence of glutathione-S-transferase (GST) from *Schistosoma japonicum*, which allows purification of the molecule in one simple affinity step by binding to glutathione-agarose beads (11). FIG. 3 shows that the GST-GCN4 polypeptides are abundant in *Escherichia coli* clones transformed with these plasmids. After one-step affinity purification, each of the GST-GCN4 polypeptides was detected as two Coomassie-blue stained bands after polyacrylamide gel electrophoresis (FIG. 3a). These purified proteins retain the ability to bind to the consensus GCN4 binding sequence as revealed by a gel retardation assay (FIG. 3b).

Hence both of the necessary affinity reagents (GST-GCN4 and avidin) are now readily available. Further, each of them can be used in an ADA test either to anchor the PCR-amplified DNA to the solid phase or to label the DNA in the aqueous phase (see below).

c. Application of the ADA to a DNA segment encoding a Human Immunodeficiency Virus (HIV) sequence.

Figure 5:
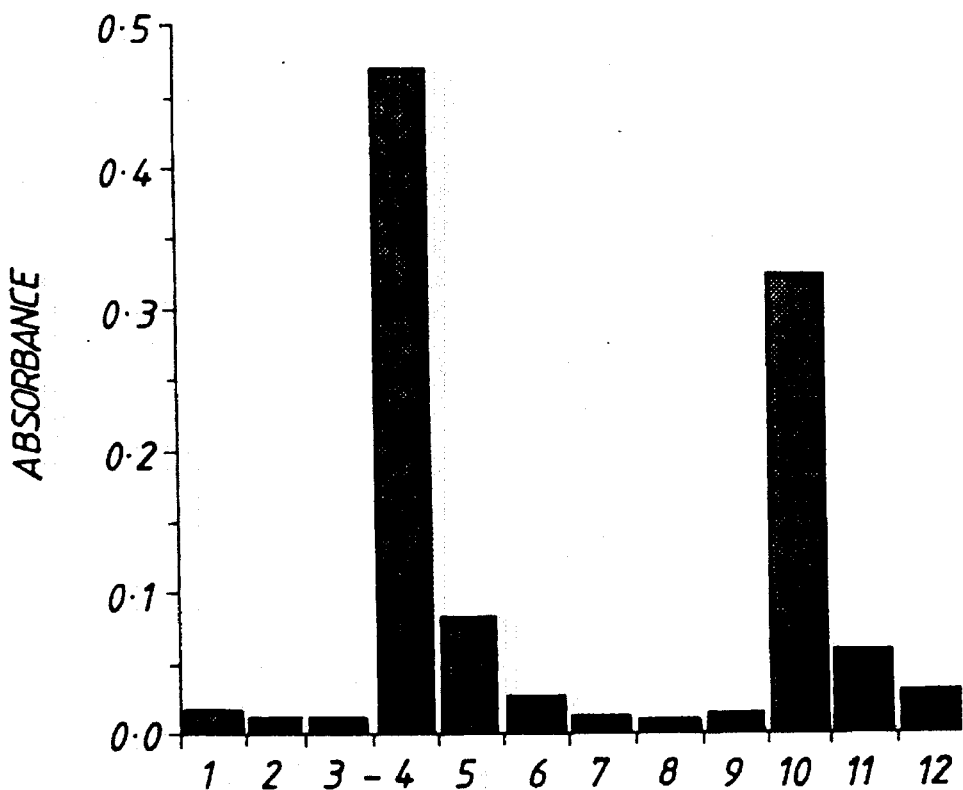
Figure 4A:
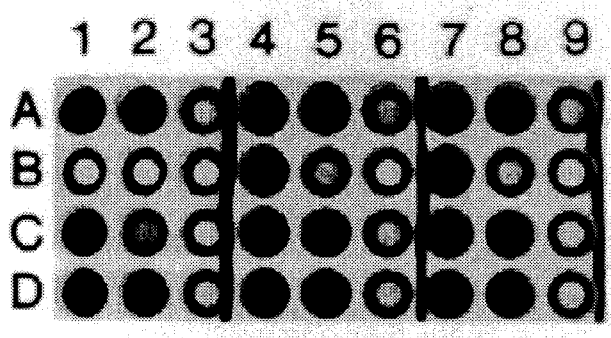
Figure 4B:
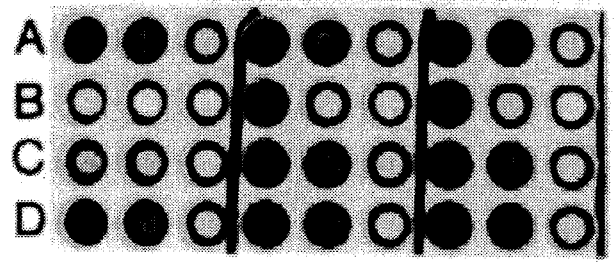

Because of the important clinical implications a region of the HIV genome was chosen as test sequence. Oligonucleotides corresponding in position to those labelled a, b, c and d in FIG. 1 were synthesised for the p24 gene of HIV and are defined in Materials and Methods. To develop the ADA, plasmid pHXBc2 bearing this gene was used initially as the test source. In initial studies to establish that the affinity reactions were feasible, DNA molecules with a biotin ligand at one end and a GCN4 binding site at the other were generated by PCR amplification of the plasmid with oligonucleotides a. and b. followed by amplification with oligonucleotides c and d. After binding these products to a microtitre well precoated with GST-GCN4 followed by washing and binding of avidin linked to peroxidase, and then washing and reaction with the chromogenic substrate, an intense reaction was observed (FIGS. 4a and 4b). This was not observed when the PCR was carried out in the absence of plasmid DNA (FIG. 5, samples 7–9).

When the amplified DNA was added to the microtitre dish in the absence of carrier DNA, the GST-GCN4 was found to bind to double-stranded DNA independently of a GCN4 binding sequence. This can be seen in row A in FIGS. 4a and 4b where oligonucleotides b. and c. (which both lack a GCN4 binding site) were used in the second step. However, this product formed with oligonucleotides b. and c. did not bind in the presence of carrier DNA (row B in FIGS. 4a and 4b, columns 1–3) whereas the corresponding products formed with oligonucleotides c. and d. (row B in FIGS. 4a and 4b, columns 4–6) or c. and d2 (row B in FIGS. 4a and 4b, columns 7–9) still bound, as indicated by the strong reaction, although this signal is lower than in row A. Intermediate levels of carrier DNA partially competed (rows C and D). It seems that GST-GCN4 3.12 and 6.8 have similar activities and specificities.

d. Application of the ADA to human cells infected with HIV.

To examine whether the ADA could detect HIV sequences specifically in DNA from infected human cells, purified DNA from persistently infected cells was used. With DNA from uninfected cells, there was no detectable signal (FIG. 5, samples 1–3) while a strong signal was obtained with DNA containing HIV (FIG. 5, samples 4–6).

EXAMPLE 3

Single Step ADA

Materials and Methods

GST-GCN4

The fused polypeptide from clone GST-GCN4 3.12 (16) was purified by binding to glutathione-agarose as described (11).

TyrR

TyrR a DNA binding protein of the "Helix turn Helix" type, and which has a C-terminal DNA binding domain was provided for testing by Dr V. Argyropolous (18).

PCR reactions

PCR reactions for amplification of p24 sequences of HIV contained 50 mM KCl, 10 mM Tris pH 8.4, 2.5 mM $MgCl_2$ 0.25 mM each dNTP, Taq polymerase (0.5 unit) and oligonucleotide primers at various concentrations. Reaction mixes (20 µl) were incubated under paraffin oil using the conditions described below. For routine use, the PCR mixes containing all components except DNA were stored as frozen aliquots.

Amplified DNA assays i) One step binding assays: Microtiter trays (Dynatech Laboratories Inc.) were coated with purified GST-GCN4 fusion polypeptides at approximately 5 µg/ml of the active product(s) in phosphate buffered saline (PBS) for 1 hr at 37° C., washed 1× and then blocked with 10% (w/v) non-fat powdered milk in PBS. The plates were then drained, but not washed, and 50 µl/well of a mixture containing 10% (w/v) non-fat powdered milk in PBS, 4 µg/ml sonicated salmon DNA, 0.05% (v/v) Tween-20 and 50 µg/ml horseradish peroxidase-avidin D conjugate (Vector Laboratories Inc.) in PBS was added. Samples of the PCR reactions (1–10 µl) were then added and allowed to react for at least 20 min at RT. Trays were washed with MTPBS-Tween-20 four times, with MTPBS four times, with $H_2O$ once, drained and then 100 ml of fresh 0.1M Na citrate, pH 4.2, containing 1 mM 2.2'-azino-bis( 3-ethylbenzthiazoline-6-sulphonic acid) (ABTS) and 0.1% (v/v) hydrogen peroxide were added to each well and absorbance read in a Titertek Multiskan MCC/340 scanner on mode 2 using filters of 414 nm and 492 nm.

ii) ADAs with GST-GCN4 immobilized on beads. The beads on the lid of a "FAST ELISA" dish (Falcon plastics) with the corners cut off were coated with GST-GCN4 by placing them in 50 µl aliquots of GST-GCN4-PBS in a microtiter tray (Dynatech Laboratories Inc.) as above for 1 hr at 37° C., and then blocked in a solution containing 10% (w/v) non-fat powdered milk, 4 µg/ml salmon DNA and 0.05% (v/v) Tween-20 in MTPBS. The lid was then flicked to drain off excess solution and the beads placed in the microtiter dish containing the PCR samples. After 20 min at RT, the beads were washed with PBS-0.05% (v/v) Tween 20. They were then reacted with 10 µg/ml peroxidase-avidin conjugate in 10% (w/v) powdered milk, 0.05% (v/v) Tween-20 in MTPBS for 20 min. They were then washed extensively with PBS and reacted with ABTS as above. Alternatively, they were reacted with 0.4 mM Tetramethylbenzidine (TMB) in 0.1M NaAc, pH 5.5 plus 1.41 mM hydrogen peroxide and read in a Titertek Multiskan MCC/340 scanner on mode 1 using filter number 7.

Oligonucleotides

Consensus oligonucleotides corresponding to sequences from the gag gene of HIV were selected after aligning available sequences from the HIV database. The oligonucleotides synthesized were:

| | | |
|---|---|---|
| a1 | ATGAGAGAACCAAGGGGAAG | |
| | (1470->1489) | |
| a2 | GGGGGACATCAAGCAGCCATGCAAATG | |
| | (1362->1388) | |
| b1 | TTGGTCCTTGTCTTATGTCCAGAATGC | |
| | (1656<-1630) | |
| b2 | ACTCCCTGACATGCTGTCATCATTTCTTC | |
| | (1846<-1818) | |
| c1 | 5'Biotin-CATAGCAGGAACTACTAGTA | |
| | (1493->1512) | |
| c2 | 5'Biotin-CAGGAACTACTAGTA | |
| | (1498->1512) | |
| d1 | AAGTGACTCAAGTGACTCAATCCTTGTCTTATGTCCAGAA | |
| | (1652<-1633) | |

-continued d2  GGATGACTCATAGGGCTATACATTC
    (1625<-1611)

DNA from HIV-infected cells

CEM cells were derived by culturing human peripheral blood cells from a patient with acute lymphoblastic leukaemia, and then infected with HIV isolate HTLV IIIb. DNA was purified using guanidine HCl and CsCl centrifugation.

DNA from clinical blood samples

DNA was purified from peripheral blood leucocytes using guanidine HCl and phenol/chloroform/ethanol centrifugation.

Plasmid DNA

Plasmid pHXBc2 (12) encoding the GAG gene of HIV was used as a source of DNA for developing the reactions. Generally, 1 ∥l of a 1 µg/ml solution per 1000 ml of PCR was used.

EXAMPLE 4

A one-step binding reaction for the ADA

Figure 6A:
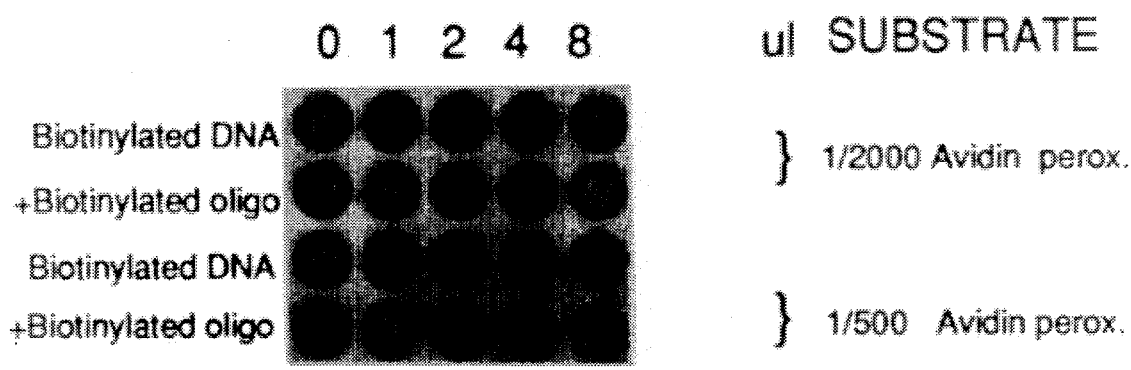
Figure 6B:
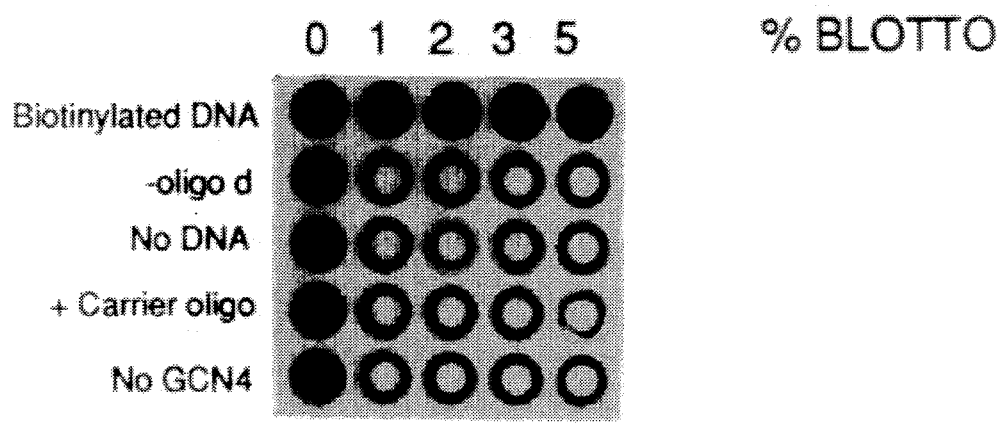

In the ADA described in Examples 1 and 2, the amplified DNA was first captured on GST-GCN4 immobilized in a microtiter well, the unincorporated substrates washed away and then avidin-peroxidase bound to the amplified DNA molecules. To simplify the procedure the amplified DNA was mixed with the avidin-peroxidase conjugate in the presence of protein and DNA carriers and these were bound to the immobilized GST-GCN4 in a single reaction mixture. Experiments with increasing amounts of the PCR sample and with PCR mix without DNA template showed that unincorporated biotinylated oligonucleotide rapidly competed out binding, as measured by the subsequent colour development after washing away the conjugate and adding substrate (FIG. 6A). By increasing the concentration of avidin and decreasing the amount of biotin, this effect could readily be overcome. However, the increased level of peroxidase raised the background. This could be prevented by blocking protein binding sites with high levels of protein carrier, for example 10% (w/v) powdered milk, after coating the wells with GST-GCN4 (FIG. 6B). Control experiments showed that it was essential to have GST-GCN4 on the plate and an appropriate target sequence on the amplified DNA (FIG. 6B).

EXAMPLE 5

Thermal separation of the two PCR steps

Because there is a very strong dependence of the thermal stability of an oligonucleotide duplex on its length, it was anticipated that it would be possible to choose lengths for oligonucleotides a, b, c and d (see page 26) such that their incorporation in a PCR would be critically dependent on the annealing temperature. If oligonucleotides a and b are considerably longer than c and d so that they form duplexes that are considerably more stable than those of c and d, then annealing at a sufficiently high temperature should prevent incorporation of c and d, allowing separation of the reactions in a mixture containing all four oligonucleotides. Preliminary studies showed unexpectedly that when different oligonucleotides 18–20 bases long were used, annealing temperatures as high as 70° C. did not prevent incorporation, although the efficiency was reduced. However, when c and that part of d complementary to the HIV sequence were 15 bases long, a clear thermal separation could be obtained at 65° C.

Figure 7A:
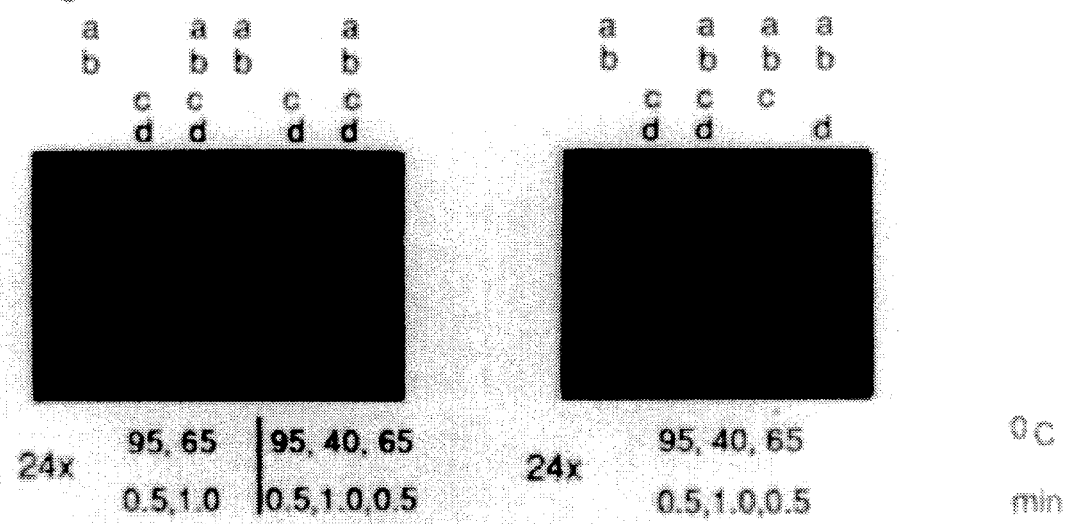

Hence, with a thermal cycling regime of only two steps per cycle, 95° C. for 1 min followed by 65° C. for 2 min (termed "without annealing") oligonucleotides a1 and b1 (20 and 28 bases long respectively) were incorporated in 24 cycles using 1 ng of plasmid DNA as the template but there was no incorporation of c2 and d2 (FIG. 7A, left panel) even with this high template input. If an annealing step of 40° C. for 1 min was introduced ("with annealing") as well as the other 2 steps, c2 and d2 could be efficiently incorporated in an additional 24 cycles (FIG. 7A, left panel). Similarly, with a total of 24 cycles all with annealing c and d were efficiently incorporated (FIG. 7A, right panel). With annealing incorporation of a1 and b1 was less efficient (FIG. 7A, right panel).

Figure 7B:
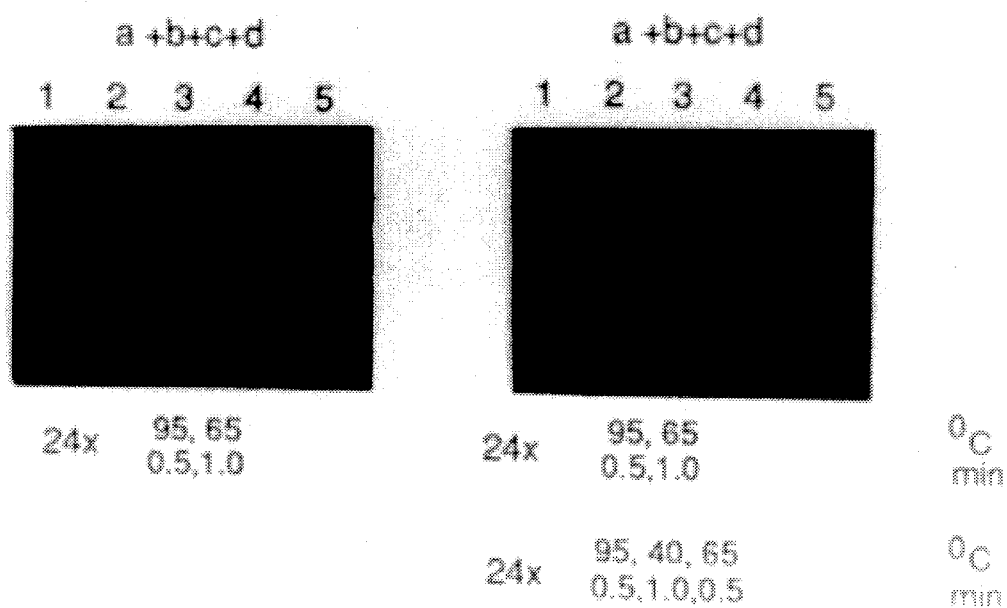

When all four oligonucleotides were included (FIG. 7A & B), only a1 and b1 were incorporated when cycled without annealing as expected. Surprisingly, however, with annealing the expected c2–d2 product was not obtained. Instead, a longer product corresponding to either a1–d2 and/or c2–b1 was obtained. Hence, it appears that either c2 or d2 or both are competed out by a1 and/or b1. In the absence of c2, this product was obtained, but in the absence of d2, it was not indicating that it is an a1–d2 product (FIG. 7A, right panel). Accordingly, the effect of lowering the relative amounts of a1 and b1 to c2 and d2 was investigated. FIG. 7B shows that when the amounts of a1 and b1 were decreased sufficiently, the expected c2–d2 product could indeed be obtained when cycled with annealing. As expected, only the a1–b1 product was formed without annealing, and the amounts of this were not greatly affected by lowering the concentrations of a1 and b1 (FIG. 7B, left panel).

ADAs on the products of these reactions were also performed (data not shown). In order for the amplified DNA to function in such an assay, it must contain a biotin moiety at one end and a GCN4 binding site at the other end. Only those reaction mixtures containing the short c–d product gave a significant colour reaction in the ADAs, confirming the structure of these molecules.

It is concluded that it is possible to separate PCR steps 1 and 2 thermally by choosing oligonucleotides of appropriate length. The products of the second reaction act as substrates in ADAs as expected. However, there is a competition effect that can readily eliminate the reaction if the concentrations of oligonucleotides a and b are not carefully controlled.

Studies with a series of dilutions of the HIV plasmid, cycled for various times under the two different temperature regimes revealed some further features of the reactions. First, it was clear that the colour intensity depended on the number of cycles both with and without annealing. However, under these conditions the sensitivity is limited: at least $10^4$ molecules are required (Example 6 below). Nevertheless, it is sensitive enough to detect HIV sequences in human DNA from persistently infected cells while the uninfected control was negative.

EXAMPLE 6

Thermal separation of the two PCRS, using more widely spaced oligonucleotides.

The apparent competition of the a and b oligonucleotides with the c and d oligonucleotides (Example 5) could result in part from steric hindrance and from kinetic effects related to the rates of annealing of the oligonucleotides. It has been noted previously (16) that this may be exacerbated by close spacing of a/c and b/d. Alternatively, c and d oligonucleotides that anneal to and are extended on the a–b template could subsequently be removed by nick translation after a second initiation event with an a or b oligonucleotide on the same template molecule in the same extension cycle. It is now clear that Taq polymerase has a 5'→3' exonuclease activity and so it can translate nicks. These effects should all be lowered if the spacing of oligonucleotides a/c and b/d are increased. Accordingly, oligonucleotides a2 and b2 were synthesized corresponding to conserved positions considerably further away from c2 and d2 than are a1 and b1.

Figure 9:
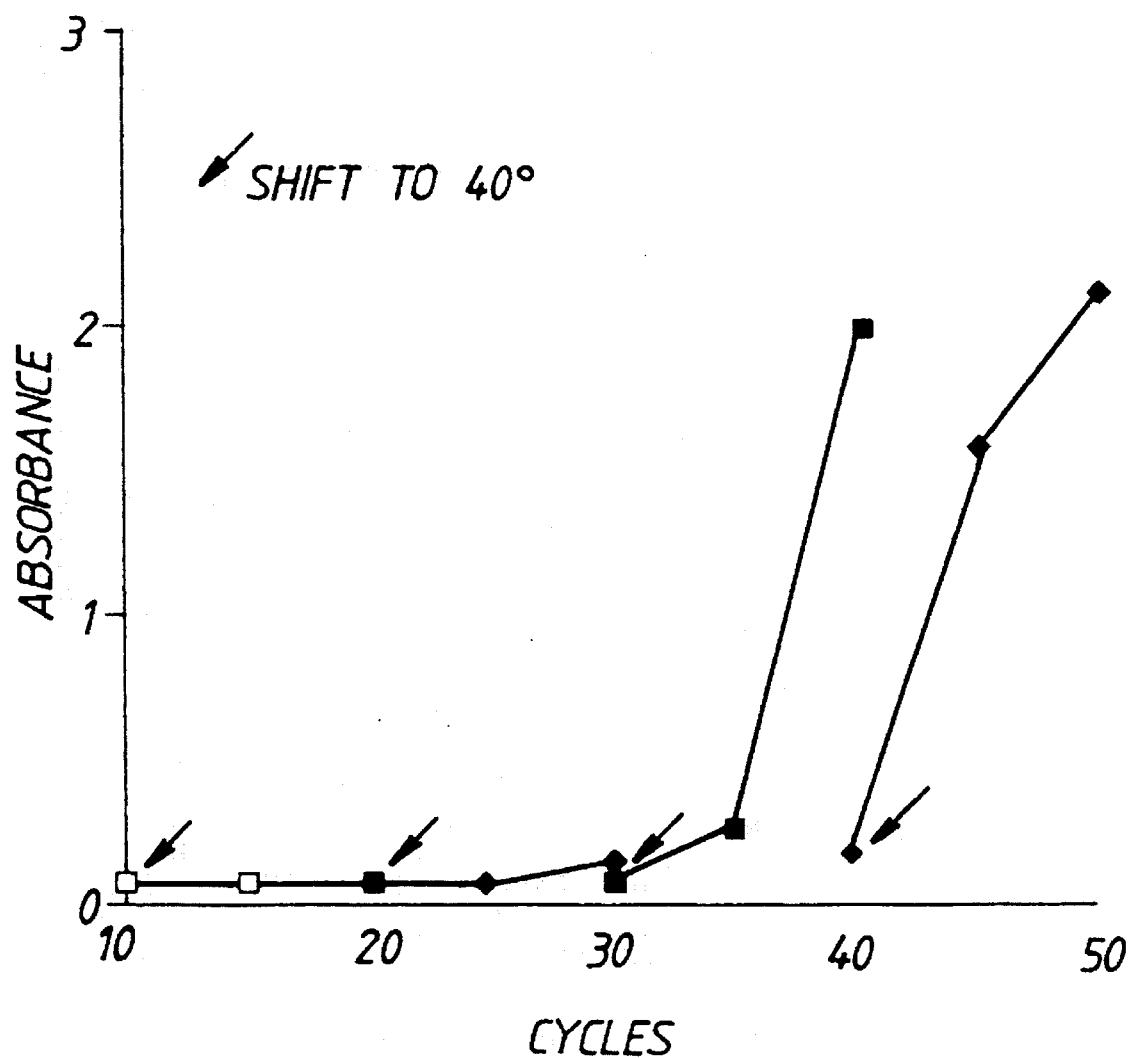

After cycling first without and then with annealing, incorporation of oligonucleotides c2 and d2 was dependent on the concentration of oligonucleotides a2 and b2 (FIG. 8a). At the optimal concentrations of a2 and b2, the c2–d2 product could be detected either by an ADA reaction or by EtBr staining from about 100 fold less input plasmid DNA than with oligonucleotides a1 and b1 (FIG. 8b). Production of the c2–d2 product and colour intensity in an ADA was dependent on the number of cycles both without and with annealing and there was no significant c2–d2 product without annealing, even after 40 cycles (FIG. 9).

Under these conditions, HIV sequences could be detected in the DNA obtained from about 250 cells from an HIV-infected CEM culture while there was no significant background even with 100-fold more DNA from uninfected cells (FIGS. 10a, 10b, 11a and 11b). It can be seen on the gel shown in FIGS. 10a and 10b that the two successive reactions with nested oligonucleotides are indeed vital to the specificity—there are many bands generated from uninfected DNA, but these do not register as positive in the ADA.

Hence, the use of a and b oligonucleotides located further out from c and d considerably increased the sensitivity with no loss of specificity.

EXAMPLE 7

Figure 12:
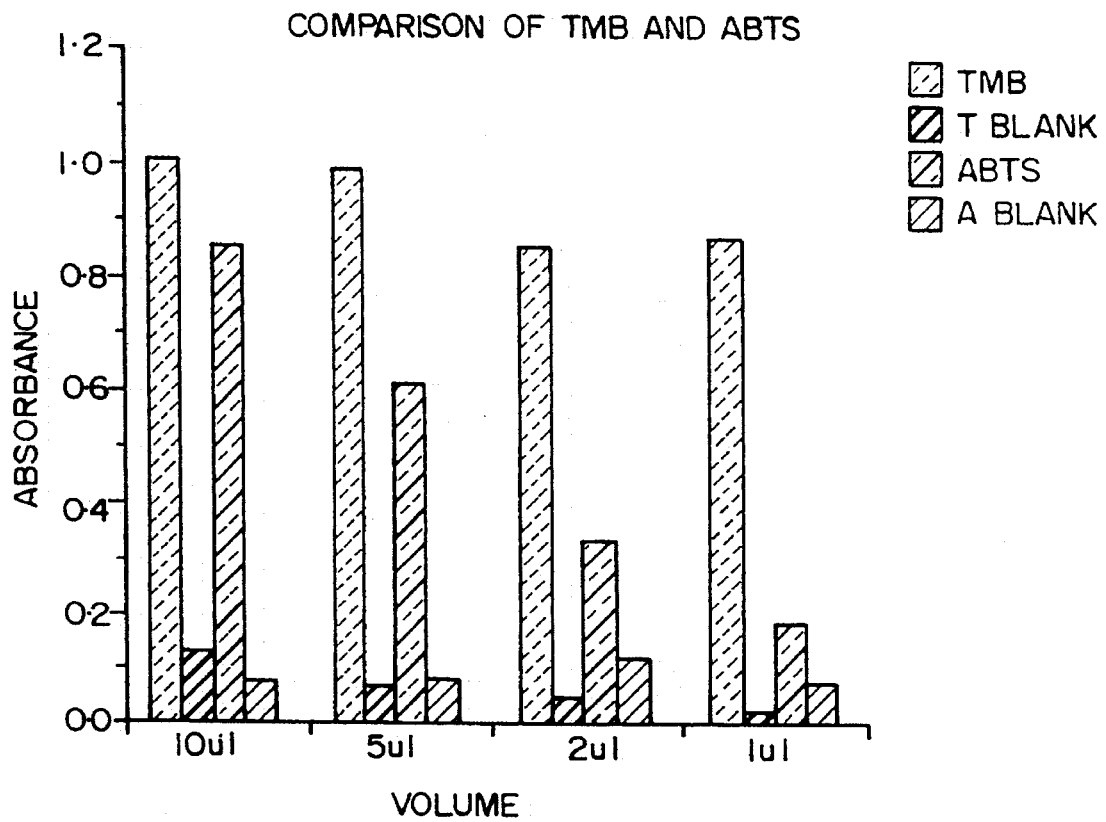
FIG. 12 shows the comparison of TMB and ABTS in an ADA mediated by GCN4-coated pins.

Development of a system for assaying PCR reactions performed in microtiter dishes One way to further simplify the ADA system is to perform the PCRs in a microtiter dish and then to capture and transfer the amplified DNA from each of the 96 wells to a second dish using an array of GST-GCN4-coated beads or pins. To test whether this was feasible, 1–10 µl samples of a PCR reaction performed with oligonucleotides c2 and d2 were made up to 20 µl in a microtiter dish and covered with a drop of paraffin oil. The beads of a FAST ELISA screening plate were coated with GST-GCN4, blocked with powdered milk-DNA and then immersed in the PCR samples for 20 min. Subsequently the beads were washed, exposed to avidin-peroxidase, washed and placed in a microtiter dish containing ABTS substrate. The responses obtained were proportional to the amount of amplified DNA (FIG. 12), and there was negligible background from equal amounts of a PCR mix incubated without substrate DNA. The colour intensity was lower by a factor of 2–3 than reactions performed using GST-GCN4-coated wells with the same material (data not shown) reflecting the lower surface area of beads. However, the sensitivity could be increased approximately 10-fold using TMB as the substrate, without any significant increase in background (FIG. 12). Hence, amplified DNA molecules can be captured and transferred efficiently using GCN4 coated beads. This is surprising given that the coated beads were first dipped through a layer of paraffin oil, mimicking the conditions necessary for a PCR.

To establish that PCR reactions could be performed in a microtiter dish and then transferred as above, reactions with oligonucleotides a1 and b1, c2 and d2 or all four oligonucleotides were set up as for FIG. 2 and incubated in the wells of a flexible microtiter dish mounted on a hollow aluminum block through which water at the appropriate temperature was circulated. The top of the block was milled to fit the bottom of the dish and zinc oxide heat-sink cream was used to ensure thermal contact. Evaporation was prevented by a drop of paraffin oil. After 24 cycles with a 40° C. annealing step, oligonucleotides a1–b1 and c2–d2 were incorporated into products of the expected size. Furthermore, the c2–d2 product gave an ADA reaction as expected (data not shown).

EXAMPLE 8

Use of another DNA binding protein, TyrR and thrombin-cleaved GCN4 in the ADA

It would be useful for some purposes to have other DNA binding proteins, with different DNA recognition sequences, that could work in an ADA reaction. For example, a set of HIV-oligonucleotides with a GST-GCN4 site could be included in the same mix as a set of hepatitis B viral oligonucleotides marked with a second DNA binding protein site, so each could be read specifically from the one PCR. TyrR is a DNA binding protein of the "Helix turn Helix" type, and which has a C-terminal DNA binding domain was provided for testing by Dr V. Argyropolous (18).

An oligonucleotide probe was manufactured which contained a TyrR recognition site and a HIV sequence, i.e. corresponding to the oligo "d" described in Example 3 except that the TyrR recognition site replaced the GCN4 binding site.

5'
TGTGTAAATATATATTTACACA/AGGGCTATACATTC
   TyrR recognition site           HIV oligo This probe was incorporated into the ADA test with the oligo "c" and reaction products tested on plates coated with GST-GCN4 or TyrR.

Figure 13:
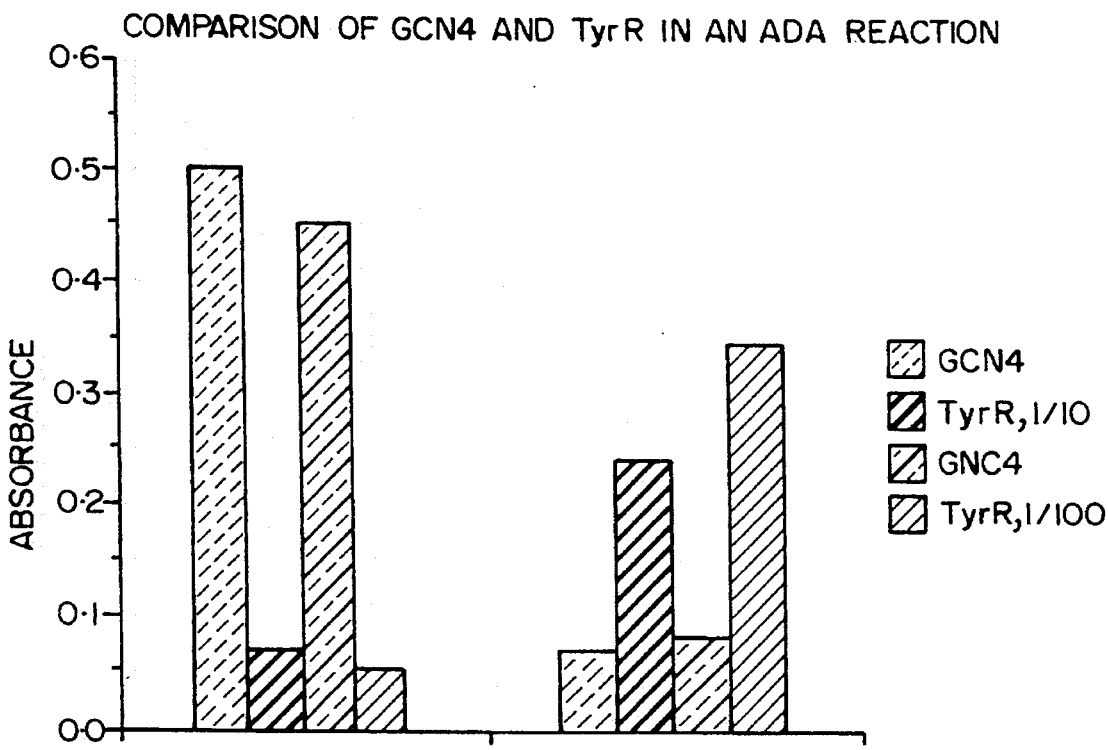
FIG. 13 shows a comparison of GCN4 and TyrR in an ADA reaction.
Figure 14:
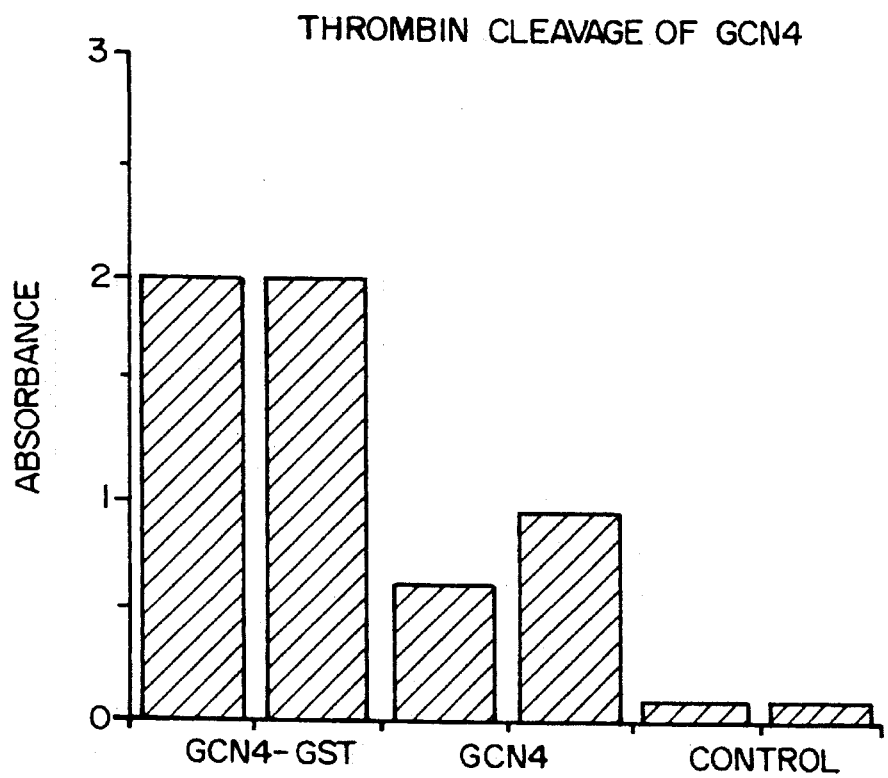
FIG. 14 shows the effect of thrombin cleavage of GCN4 in the ADA.

Results were compared with those of the same experiment but using the original oligo "d" containing the GST-GCN4 binding site as shown in FIG. 13.

EXAMPLE 9

Clinical Trial

The following example shows the results of a clinical trial performed on Peripheral Blood Lymphocytes (PBL's) taken from patients positively diagnosed as suffering from AIDS or from negative controls. The trial was performed blind.

The PBL's were prepared from blood samples by lysis in Guanidine thiocyanate buffer (4M) and centrifugation.

DNA was extracted and purified from PBL's using the same technique of Guanidine thiocyanate centrifugation.

One step ADA reactions were performed using oligos a2, b2, c2 and d2 as described in Example 3.

The legend for the results provided in FIG. 15 is as follows:

− No DNA

DO Human DNA (negative control)

CC Positive control using CEM cells transfected with HIV

CP Positive control using Plasmid DNA

+ Positive control using CEM cells having Plasmid DNA incorporated therein.

20–55 Clinical specimens
Samples 20 and 46 were obtained from healthy humans.
The results clearly show the sensitivity and specificity of the ADA to detect HIV.

EXAMPLE 10

Detection of *Mycoplasma pneumoniae* using the ADA

This example shows that the ADA can be used to detect DNA from *M. pneumoniae*, a pathogen which can cause severe respiratory tract infections. The first experiment used plasmid DNA containing the P1 gene of *M. pneumoniae* as described in Hu et al, *Gene*, 64,217, and one pair of ADA primers. The second experiment used clinical specimens (nasopharyngeal aspirate) to which had been added whole *M. pneumoniae* cells, and two nested pairs of primers.

(i) This experiment used only one pair of ADA primers, one of them being biotinylated, and the other containing the GCN4 recognition sequence, as follows:

ADA primer 1: 5'biotinyl-TCAAAACAACGACAC-3' (corresponding to nucleotides 3863–3877 of the P1 gene)

ADA primer 2: 5'-GGATGACTCATTTCAGAAAGTC-GAC-3' (corresponding to nucleotides 4144–4100 of the P1 gene; the first 10 nucleotides constitute the GCN4 site)

The ADA consisted of taking purified P1 plasmid DNA and adding 0.6 µmolar/120 ng of each of ADA primers 1 and 2. The first 5 cycles of amplification were conducted as follows: 94° C.—1 minute (melting); 37° C.—2 minutes (annealing); 60° C.—3 minutes (extension). The next 25 cycles were: 90° C.—1 minute; 37° C.—2 minutes; 60° C.—3 minutes; with the final extension at 72° C. for 10 minutes.

Approximately ⅓ of the product was then analysed in a one step binding reaction in which microtitre plates were coated with GST-GCN4 (250 ng/well in PBS) overnight at 4° C. Detection of amplified DNA was performed as previously described. In the second part of this experiment, a smaller (i.e. ⅒) amount of DNA was used as starting material.

The mixture used for performing the PCR was:
2 units Taq polymerase (Cetus),
10 mM Tris HCl pH 8.3,
50 mM KCl,
1.5mM $MgCl_2$,
0.2% µmolar dNTP's,
plus ADA primers as above, in a volume of 50 µl.

(ii) This experiment used 2 pairs of primers—the ADA primers described above and another pair, the PCR primers, which lie outside the ADA primers, as follows:

PCR primer 1: 5'-CAAGCCAAACACGAGCTCCG-GCC-3' (corresponding to nucleotides 3666–3688 of the P1 gene)

PCR primer 2: 5'-CCAGTGTCAGCTGTTTGTCCTTC-CCC-3' (corresponding to nucleotides 4208–4183 of the P1 gene)

Various amounts of whole *M. pneumoniae* cells were added to nasopharyngeal aspirate and the amount of cells added measured as the approximate number of genomes. The material was centrifuged and the precipitate collected. This was treated with proteinase K (30 µl, 200 µg/ml in 10 mM Tris CL pH 8.3) at 37° C./1 hour to free the DNA, then at 95° C./15 minutes to inactivate the proteinase K. The ADA was then conducted as described below.

The PCR mixture used was as for experiment (i), except that it included 250 ng of each ADA primer and 5 ng of each PCR primer.

The first round of cycling (i.e. that which favoured the PCR primers) comprised 30 cycles as follows: 94° C.—1 minute; 65° C.—2 minutes; 72° C.—3 minutes. The second round, for the ADA primers, comprised 15 cycles as follows: 90° C.—1 minute; 40° C.—1 minute; 60° C.—3 minutes; followed by a final extension step at the end of 72° C. for 10 minutes.

Analysis and detection of the amplified DNA was performed in the same manner as in experiment (i).

(iii) The results obtained in experiments (i) and (ii) are set out in the following tables (in which the results are scored using a plus(+) scale, with maximum colour being ++++ and no colour being –):

| Experiment (i) | |
|---|---|
| Amount of plasmid DNA | Result |
| 56 ng ($7 \times 10^8$ molecules) P1 plasmid: | ++ |
| 5.6 ng ($6 \times 10^7$ molecules) P1 plasmid: | + |
| No plasmid control | – |

| Experiment (ii) | |
|---|---|
| Approx no. of *M. pneumoniae* genomes | Result |
| $5 \times 10^8$ | +++ |
| $2.5 \times 10^8$ | + |
| $10^8$ | ++ |
| $10^7$ | +/– |
| $5 \times 10^5$ | – |
| $2.5 \times 10^5$ | – |
| $10^5$ | – |
| $10^4$ | – |
| 0 | – |

REFERENCES

1. Saiki, R. K., Scharf, S., Faloona, F., Mullis, K. B., Horn, G. T., Erlich, H. A. and Arnheim, N. (1985) *Science* 2.30, 1350–1354.
2. Saiki, R. K., Gelfand, D. H., Stoffel, S., Scharf, S. J., Higuchi, R., Horn, G. T., Mullis, K. B. and Erlich, H. A. (1987) *Science* 239, 487–491.
3. Lee, C. C., Wu, X., Gibbs, R. A., Cook, R. G., Muzny, D. M. and Caskey, C. T. (1988) *Science* 239, 1288–1291.
4. Gyllensten, U. B. and Erlich, H. A. (1988) *Proc. Natl. Acad. Sci. USA* 85, 7652–7656.
5. Triglia, T., Peterson, M. G. and Kemp, D. J. (1988) *Nuc. Acids Res.* 16, 8186.
6. Kim, H-S. and Smithies, O. (1988) *Nuc.Acids Res.* 16, 8887–8904.
7. Landegren, U., Kaiser, R., Caskey, C. T. and Hood, L. (1988) *Science* 242, 229–237.
8. Laure, F., Rouziox, C., Veber, F., Jacomet, C., Courgnaud, G., Blanche, S., Burgard, M., Griscelli, C. and Brechot, C. (1988) *The Lancet,* 538–541.
9. Hinnebusch, A. G. (1984) *Proc. Natl. Acad. Sci. USA* 81, 6442–6446.
10. Hope, I. A. and Struhl, K. (1986) *Cell* 46, 885–894.
11. Smith, D. B. and Johnson, K. S. (1988) *Gene* 67, 31–40.
12. Sodroski, J., Patarca, R., Rosen, C., Weng-Staah, F. and Haseltine, W. (1985) *Science* 229, 74–77; Sanchez-Pescadon, R., Power, M. D., Bart, P. J., Steinmer, K. S., Stempien, M. M., Brown-Shimer, S. L., Gee, W. W., Renard, A., Randolph, A., Levy, I. A., Dina, D. and Luciw, P. A. (1985) *Science* 227, 484–492.

13. Kemp, D. J., Coppel, R. L. and Anders, R. F. (1987) *Ann. Rev. Microbiol.* 41, 181–208.
14. Hill, D. E., Hope, I. A., Macke, J. P. and Struhl, K. (1986) *Science* 234, 451–457.
15. Hope, I. A. and Struhl, K. (1985) *Cell* 43, 177–188.
16. Kemp, D. J., Smith, D. B., Foote, S. J., Samaras, N. and Peterson, M. G. (1989). *Proc. Natl. Acad. Sci. USA* 86, 2423–2427
17. Hinnebusch, A. G. (1984) *Proc. Natl. Acad. Sci. USA* 81, 6442–6446.
18. Argyropolous, V. (1989) Thesis for Doctor of Philosophy, The University of Melbourne, Parkville, Victoria, Australia.
19. Struhl K. (1989) *Trends in Biological Sciences*, 14, 137.

We claim:

1. A method for capturing target DNA on a solid substrate comprising: a) amplifying said target DNA by a polymerase chain reaction with a pair of oligonucleotide primers which are complementary to said target DNA wherein one of the primers comprises a nucleotide sequence which is a ligand for a double stranded DNA-binding protein when said nucleotide sequence is incorporated into said amplified target DNA; and b) contacting said amplified target DNA with a double stranded DNA-binding protein immobilized on a solid substrate.

2. The method according to claim 1 wherein the double stranded DNA binding protein is of the leucine zipper type.

3. The method according to claim 1 wherein said DNA binding protein comprises a DNA binding domain of GCN4.

4. The method according to claim 1 wherein the DNA binding protein is GST-GCN4.

5. The method according to claim 1 wherein the double stranded DNA-specific DNA binding protein is of the helix turn helix type.

6. A method for capturing target DNA on a solid substrate which comprises:

a) amplifying said target DNA by a first polymerase chain reaction with a first pair of oligonucleotide primers which are complementary to said target DNA to provide amplified target DNA;

b) additionally amplifying said amplified target DNA by a second polymerase chain reaction with a second pair of oligonucleotide primers which are complementary to said target DNA and are nested between said first pair or primers, wherein one of said second pair of primers comprises a nucleotide sequence which is recognized by a double stranded DNA-binding protein when said nucleotide sequence is incorporated into said additionally amplified target DNA; and c) contacting said additionally amplified target DNA with a double stranded DNA-binding protein immobilized on a solid substrate.

7. The method according to claim 6 wherein said polymerase chain reaction using a first set of oligonucleotide primers and said polymerase chain reaction using a second set of oligonucleotide primers are performed in a single reaction mixture.

8. The method according to claim 6 wherein said double stranded DNA binding protein is of the leucine zipper type.

9. The method according to claim 6 wherein said double stranded DNA binding protein comprises a DNA binding domain of GCN4.

10. The method according to claim 6 wherein said double stranded DNA binding protein is GST-GCN4.

11. The method according to claim 6 wherein said double stranded DNA binding protein is of the helix turn helix type.

12. A method for the detection of target DNA in a sample which comprises:

a) amplifying said target DNA by a polymerase chain reaction with a pair of oligonucleotide primers which are complementary to said target DNA wherein one of said primers comprises a nucleotide sequence which is recognized by a double stranded DNA-binding protein when said nucleotide sequence is incorporated into amplified target DNA and the other of said primers comprises a covalently bound molecule capable of being detected;

b) contacting said amplified target DNA with a double stranded DNA-binding protein immobilized on a solid substrate such that an association forms between said amplified target DNA and said immobilized double stranded DNA-binding molecule; and c) detecting said covalently bound molecule which has associated with said double stranded DNA-binding protein immobilized on said solid substrate to indicate the presence of said amplified target DNA bound to said solid substrate.

13. The method according to claim 12 which further comprises contacting the amplified target DNA simultaneously with a detection complex.

14. The method according to claim 12 wherein the double stranded DNA binding protein is of the leucine zipper type.

15. The method according to claim 13 wherein said DNA binding protein comprises a DNA binding domain of GCN4.

16. The method according to claim 12 wherein the DNA binding protein is GST-GCN4.

17. The method according to claim 12 wherein the double stranded DNA-specific DNA binding protein is of the helix turn helix type.

18. A method for detecting target DNA in a sample which comprises:

a) amplifying said target DNA by a first polymerase chain reaction with a first pair of oligonucleotide primers which are complementary to said target DNA to provide amplified target DNA;

b) additionally amplifying said amplified target DNA by a second polymerase chain reaction with a second pair of oligonucleotide primers which are complementary to said target DNA and are nested between the primers of said first pair and wherein one of the primers of said second set comprises a nucleotide sequence which is recognized by a double stranded DNA-binding protein when said nucleotide sequence is incorporated into said additionally amplified target DNA and the other of said primers of said second set comprises a covalently bound molecule capable of being detected;

c) contacting said additionally amplified target DNA with a double stranded DNA-binding protein immobilized on a solid substrate such that an association forms between said additionally amplified target DNA and said immobilized double stranded DNA-binding molecule; and d) detecting said covalently bound molecule which has associated with said double stranded DNA-binding protein immobilized on said solid substrate to indicate the presence of said additionally amplified target DNA bound to said solid substrate.

19. The method according to claim 18 wherein said polymerase chain reaction using a first set of oligonucleotide primers and said polymerase chain reaction using a second set of oligonucleotide primers are performed in a single reaction mixture.

20. The method according to claim 18 which further comprises contacting the additionally amplified DNA simultaneously with a detection reagent for said covalently bound molecule.

21. The method according to claim 18 wherein the double stranded DNA binding protein is of the leucine zipper type.

22. The method according to claim 18 wherein said DNA binding protein comprises a DNA binding domain of GCN4.

23. The method according to claim 18 wherein said DNA binding protein is GST-GCN4.

24. The method according to claim 18 wherein the double stranded DNA binding protein is of the helix turn helix type.

25. A method for capturing HIV DNA on a solid substrate comprising: a) amplifying said HIV DNA by a polymerase chain reaction with a pair of oligonucleotide primers which are complementary to said HIV DNA wherein one of the primers comprises a nucleotide sequence which is a ligand for a double stranded DNA binding protein when said nucleotide sequence is incorporated into said amplified HIV DNA; and b) contacting said amplified HIV DNA with a double stranded DNA-binding protein immobilized on a solid substrate.

26. A method for capturing HIV DNA on a solid substrate comprising: a) amplifying said HIV DNA by a first polymerase chain reaction with a first pair of oligonucleotide primers which are complementary to HIV DNA to provide amplified HIV DNA; b) additionally amplifying said amplified HIV DNA by a second polymerase chain reaction with a second pair of oligonucleotide primers which are complementary to said HIV DNA and are nested between said first pair of primers wherein one of said second pair of primers comprises a nucleotide sequence which is recognized by a double stranded DNA-binding protein when said nucleotide sequence is incorporated into said additionally amplified HIV DNA; and c) contacting said additionally amplified HIV DNA with a double stranded DNA-binding protein immobilized on a solid substrate.

27. A method for the detection of HIV DNA in a sample which comprises: a) amplifying said HIV DNA by a polymerase chain reaction with a pair of oligonucleotide primers which are complementary to said HIV DNA wherein one of said primers comprises a nucleotide sequence which is recognized by a double stranded DNA-binding protein when said nucleotide sequence is incorporated into amplified HIV DNA and the other of said primers comprises a covalently bound molecule capable of being detected; b) contacting said amplified HIV DNA with a double stranded DNA-binding protein immobilized on a solid substrate such that an association forms between said amplified HIV DNA and said immobilized double stranded DNA-binding molecule; and c) detecting said covalently bound molecule which has associated with said double stranded DNA-binding protein immobilized on said solid substrate to indicate the presence of said amplified HIV DNA bound to said double stranded DNA binding protein immobilized on said solid substrate.

28. A method for detecting HIV DNA in a sample which comprises: a) amplifying said HIV DNA by a first polymerase chain reaction with a first pair of oligonucleotide primers which are complementary to said HIV DNA to provide amplified HIV DNA; b) additionally amplifying said amplified HIV DNA by a second polymerase chain reaction with a second pair of oligonucleotide primers which are complementary to said HIV DNA and are nested between the primers of said first pair and wherein one of the primers of said second set comprises a nucleotide sequence which is recognized by a double stranded DNA-binding protein when said nucleotide sequence is incorporated into said additionally amplified HIV DNA and the other of said primers of said second set comprises a covalently bound molecule capable of being detected; c) contacting said additionally amplified HIV DNA with a double stranded DNA-binding protein immobilized on a solid substrate such that an association forms between said additionally amplified HIV DNA and said immobilized double stranded DNA-binding protein; and d) detecting said covalently bound molecule which has associated with said double stranded DNA-binding protein immobilized on said solid substrate to indicate the presence of said additionally amplified HIV DNA bound to said solid substrate.

29. The method according to any one of claims 12, 24, 20–23 and wherein said covalently bound molecule is biotin which is detected using a detection reagent comprising avidin/peroxidase.

30. The method according to any one of claims 1–28 wherein said solid substrate is a well of a microtiter dish.

31. A test kit for detecting target DNA in a sample comprising in compartmental form, a container for receiving said target DNA which contains reagents for a polymerase chain reaction comprising a pair of oligonucleotide primers wherein one of the primers comprises a nucleotide sequence which is a ligand for a sequence specific double stranded DNA-binding protein; and a solid substrate coated with said double stranded DNA-binding protein.

32. A test kit for detecting target DNA in a sample comprising in compartmental form, a container for said target DNA which contains reagents for two polymerase chain reactions including a first and second pair of oligonucleotide primers wherein one of the primers comprises a nucleotide sequence which is a ligand for a sequence specific double stranded DNA-binding protein; and a solid substrate coated with said double stranded DNA-binding protein.

33. A test kit for detecting target DNA in a sample comprising in compartmental form, a first container for receiving said target DNA which contains reagents for a first polymerase chain reaction including a first pair of oligonucleotide primers; a second container containing a second pair of oligonucleotide primers and reagents for a second polymerase chain reaction wherein one of the primers comprises a nucleotide sequence which is a ligand for a sequence specific double stranded DNA-binding protein; and a solid substrate coated with said double stranded DNA-binding protein.

34. The kit according to any one of claims 31, 32 and 33 wherein said double stranded DNA-binding protein is of the leucine zipper type.

35. The kit according to claim 34 wherein said double stranded DNA binding protein comprises a DNA binding domain of GCN4.

36. The kit according to claim 34 wherein said double stranded DNA-binding protein is GST-GCN4.

37. The kit according to any one of claim 31, 32 and 33 wherein said double stranded DNA binding protein is of the helix turn helix type.

38. The kit according to any one of claims 31, 32 and 33 which further comprises a detection reagent.

* * * * *

UNITED STATES PATENT AND TRADEMARK OFFICE
CERTIFICATE OF CORRECTION

PATENT NO. : 5,536,648
DATED : July 16, 1996
INVENTOR(S) : David J. Kemp, et al.

It is certified that error appears in the above-identified patent and that said Letters Patent are hereby corrected as shown below:

Column 4, line 17: " µ/ml " should read -- µg/ml --

Column 5, line 3: " g/ml " should read -- µg/ml --

Column 15, line 17: " 1\\1 " should read -- 1 µl --

Column 18, line 34: insert --The probe was of the sequence--

Signed and Sealed this

First Day of July, 1997

Attest:

BRUCE LEHMAN

Attesting Officer     Commissioner of Patents and Trademarks